(12) United States Patent
Akin et al.

(10) Patent No.: US 6,458,140 B2
(45) Date of Patent: *Oct. 1, 2002

(54) DEVICES AND METHODS FOR INTERCONNECTING VESSELS

(75) Inventors: Jodi Akin, Alamo; Amr Salahieh, Campbell, both of CA (US); Michael Mack, Dallas, TX (US); Hani Shennib, Quebec (CA); Jackson Demond, Santa Cruz, CA (US); Ronald K. Yamamoto, San Francisco, CA (US); Stanley R. Conston, San Carlos, CA (US)

(73) Assignee: Vasconnect, Inc., Walnut Creek, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/771,007

(22) Filed: Jan. 26, 2001

Related U.S. Application Data

(63) Continuation-in-part of application No. PCT/US00/20588, filed on Jul. 28, 2000, which is a continuation-in-part of application No. 09/363,309, filed on Jul. 28, 1999, now Pat. No. 6,251,116, and a continuation-in-part of application No. 09/363,310, filed on Jul. 28, 1999, now Pat. No. 6,165,185.

(51) Int. Cl.⁷ .............................................. A61B 17/04

(52) U.S. Cl. ........................ 606/153; 606/154; 606/155

(58) Field of Search ................................ 606/139, 153, 606/154, 155

(56) References Cited

U.S. PATENT DOCUMENTS

| | | | |
|---|---|---|---|
| 4,352,358 A | * | 10/1982 | Angelchik .................. 606/153 |
| 5,141,516 A | | 8/1992 | Detweiler |
| 5,620,461 A | | 4/1997 | Muijs van de Moer et al. |
| 5,797,934 A | | 8/1998 | Rygaard |
| 5,868,763 A | | 2/1999 | Spence et al. |
| 5,921,995 A | | 7/1999 | Kleshinski |
| 6,007,544 A | | 12/1999 | Kim |
| 6,007,576 A | | 12/1999 | McClellan |
| 6,056,762 A | | 5/2000 | Nash et al. |
| 2001/0004699 A1 | | 6/2001 | Gittings et al. |

FOREIGN PATENT DOCUMENTS

| | | |
|---|---|---|
| EP | 0894475 A1 | 2/1999 |
| WO | WO 98/02099 | 1/1998 |
| WO | WO 98/16174 | 4/1998 |

(List continued on next page.)

*Primary Examiner*—Gary Jackson
(74) *Attorney, Agent, or Firm*—Carol LaSalle; Bozicevic, Field & Francis LLP

(57) ABSTRACT

The present invention provides implantable devices and associated methods for interconnecting human vessels in a side-to-side or an end-to-side arrangement rapidly, safely and in a minimally invasive manner. The devices comprises at least a first segment, a second component, and a flow opening between the at least one segment and the second component when operatively used. The first segment is flexible and has physical and mechanical properties which allow it to be easily inserted into a vessel, to conformably seal with the inside wall of the vessel and to be resistant to dislodging from the vessel. The second component may comprise a second segment having the same or a similar configuration as the first segment or may be a tubular member which extends from the first segment. The first and second segments are flexible for easy insertion into an incision made within the side of each vessel. Upon release from a constricted state, each flexible segment subsequently conforms to the interior walls of a vessel to provide a sealing contact along the contact surface of the segment inserted within. The tubular member is configured to be inserted into a transected end of a vessel. The flow opening provides fluid interconnectivity between the vessels connected by the implanted devices. The devices are configured so as to: (1) not impede flow inside a vessel; (2) prevent leakage from the incisions within the vessels; and (3) apposition the vessels toward each other allowing the vessels to heal together so that flow in one vessel may flow to the other.

32 Claims, 10 Drawing Sheets

FOREIGN PATENT DOCUMENTS

| WO | WO 98/40036 | 9/1998 |
| WO | WO 98/52471 | 11/1998 |
| WO | WO 99/08603 | 2/1999 |
| WO | WO 99/48427 | 9/1999 |
| WO | WO 00/41633 | 7/2000 |

* cited by examiner

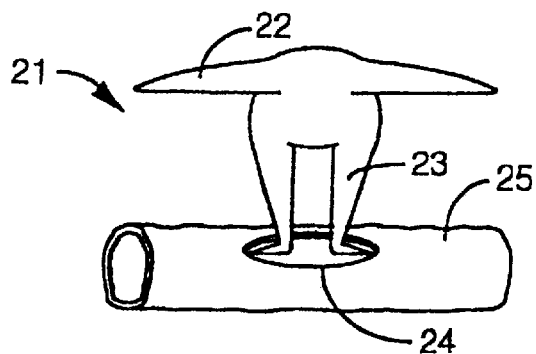
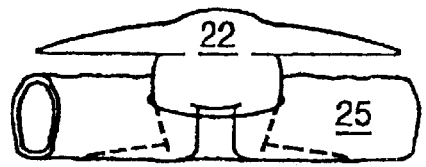
FIG. 4A  FIG. 4B
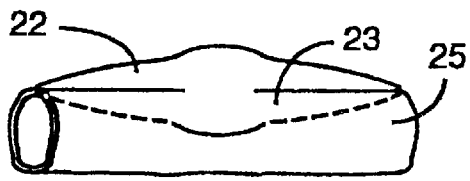
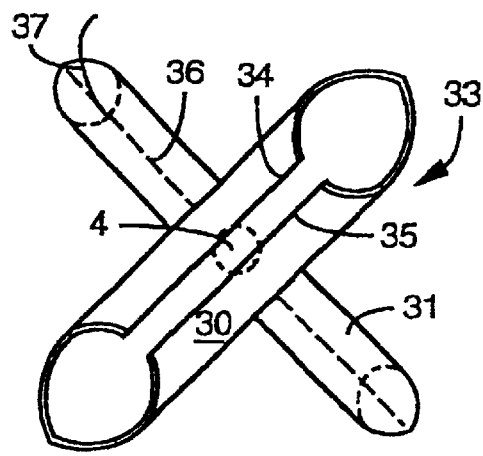
FIG. 4C  FIG. 5

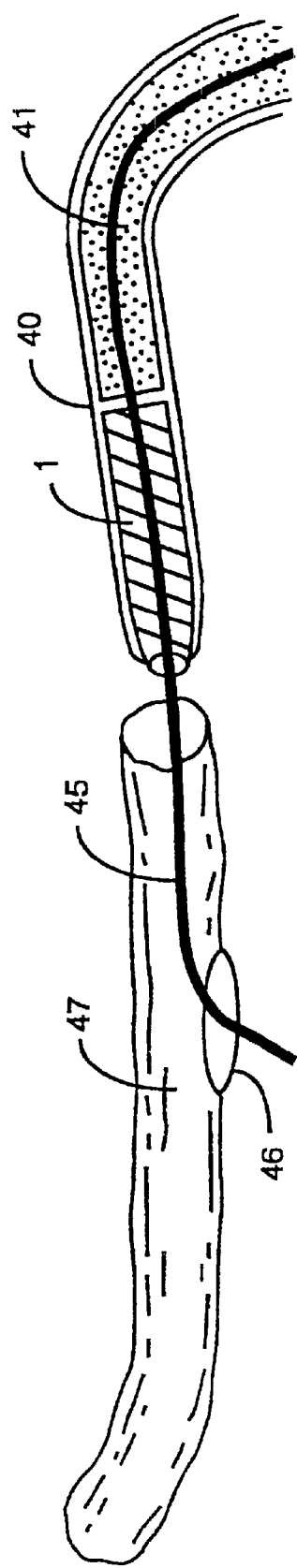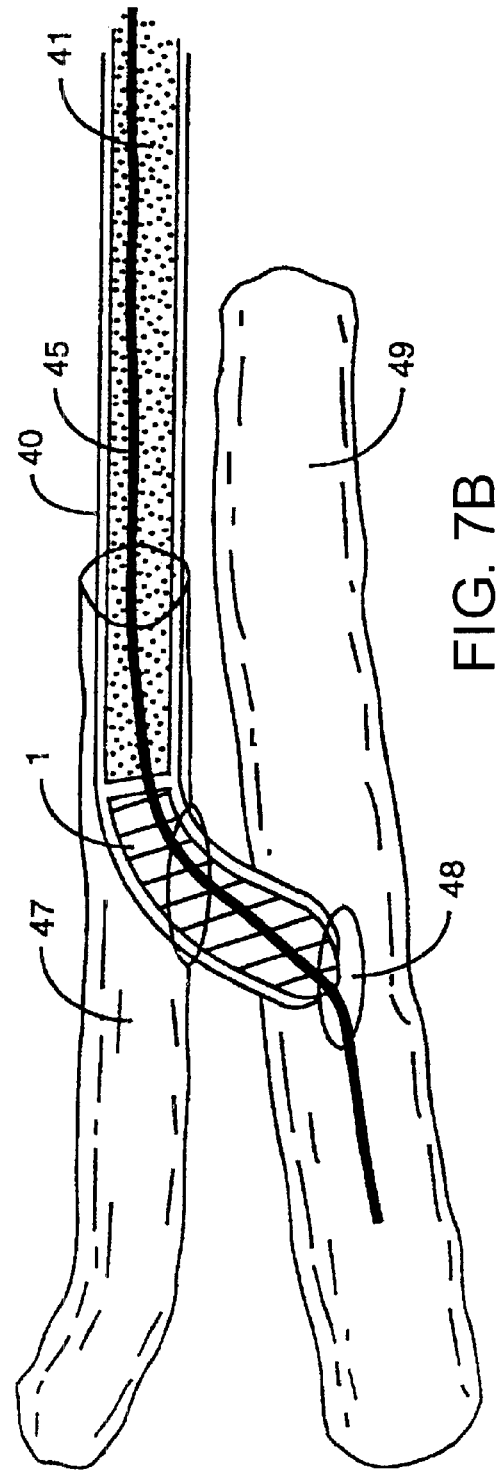
FIG. 7A
FIG. 7B

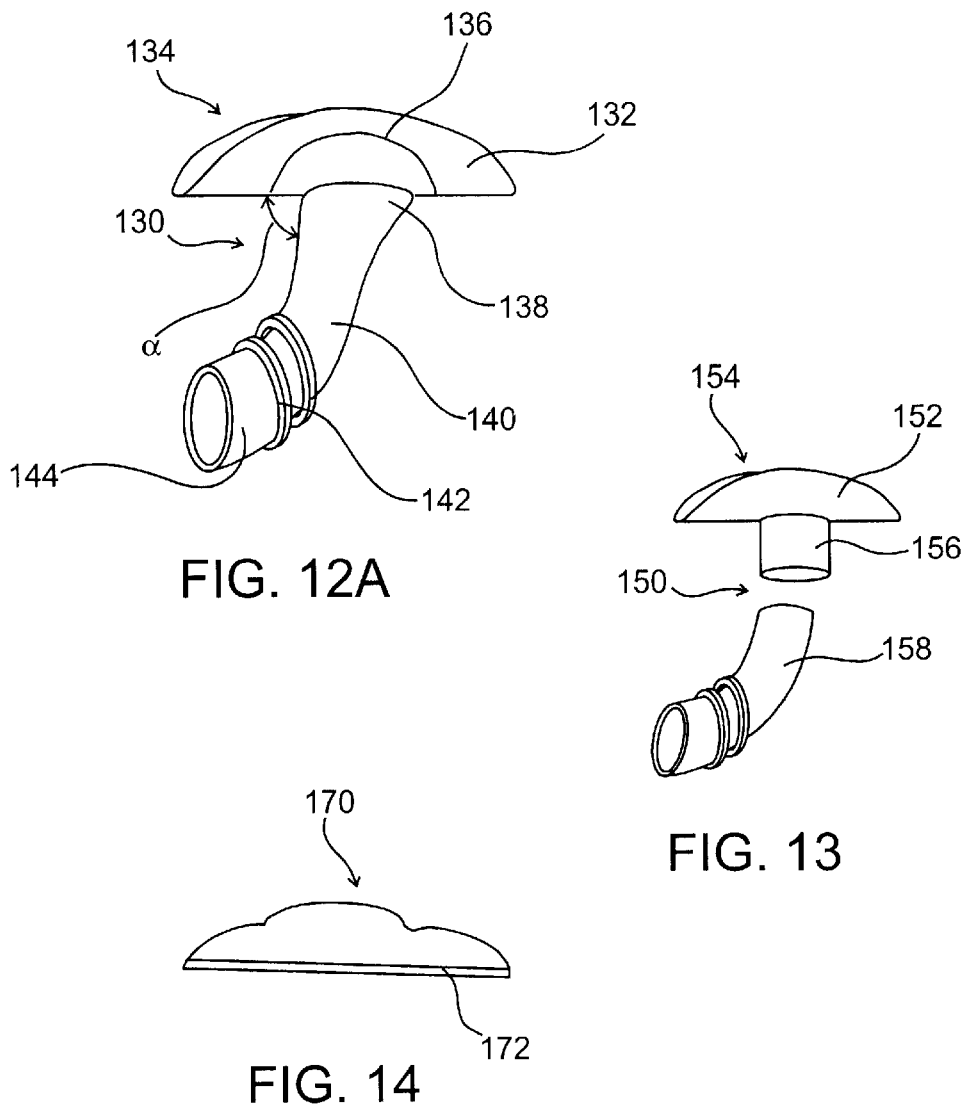
FIG. 12A
FIG. 13
FIG. 14
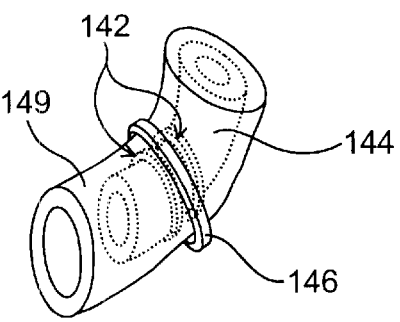
FIG. 12B

DEVICES AND METHODS FOR INTERCONNECTING VESSELS

CROSS-REFERENCE TO RELATED APPLICATIONS

This application is a continuation-in-part of application Ser. no. PCT/US00/20588 filed on Jul. 28, 2000; which application is a continuation-in-part of application Ser. No. 09/363,309 filed on Jul. 28, 1999 now U.S. Pat. No. 6,251,116 and application Ser. No. 09/363,310 filed on Jul. 28, 1999, now U.S. Pat. No. 6,165,185 issued on Dec. 26, 2000; the disclosures of which are herein incorporated by reference.

INTRODUCTION

1. Technical Field

The field of this invention is anastomosis and anastomotic devices.

2. Background of the Invention

The human body has numerous vessels carrying fluid to essential tissues and areas for recirculation or excretion. When vessels become damaged, severed or wholly occluded due to physiological problems, certain sections must be bypassed to allow for the free and continuous flow of fluids. Anastomosis is performed for the purpose of connecting different conduits together to optimize or redirect flow. In cardiac surgery, anastomosis is done to bypass the occluded vessel by harvesting a member of an unobstructed vessel and joining it to the occluded vessel below the point of stenosis.

The common procedure for performing the anastomosis during bypass surgery requires the use of very small sutures, loupes and microsurgical techniques. Surgeons must delicately sew the vessels together being careful not to suture too tightly so as to tear the delicate tissue, thereby injuring the vessel which may then result in poor patency of the anastomosis. Recently, some surgeons have used staples and associated stapling mechanisms and techniques to form an anastomosis, but many of the same difficulties and problems have presented themselves. Basically, the tension and/or compression forces exerted on the vessel walls as a result of suturing and stapling can result in damage to the vessel wall, even to the extent of causing tissue necrosis. Damage to the intima of a vessel is particularly problematic as it may inhibit the natural bonding process that occurs between the anastomized vessels and which is necessary for sufficient patency. Futhermore, damaged vessel walls are likely to have protuberances that when exposed to the bloodstream could obstruct blood flow or may produce turbulence which can lead to formation of thrombus, stenosis and possible occlusion of the artery.

As cardiac surgery is moving into less invasive procedures, surgical access is being reduced, forcing surgeons to work in constantly smaller surgical fields. The procedures are made more difficult due to the multiple characteristics that are unique to each anastomosis and to each patient. For example, the arteries' internal diameter dimensions are difficult to predict and the inside walls are often covered with deposits of stenotic plaque which creates the risk of dislodging plaque into the patient's blood stream during the anastomosis procedure. The resulting emboli in turn create a greater risk of stroke for the patient. The dislodgement of plaque is most likely to occur when the vessel wall undergoes trauma such as the puncturing, compression and tension exerted on the vessel by suturing and stapling. The vessel walls can also be friable and easy to tear, and are often covered with layers of fat and/or are deeply seated in the myocardium, adding to the difficulty of effectively and safely performing conventional anastomotic procedures.

Cardiac surgeons sometimes inadvertently suture too loosely, resulting in leakage of fluid from the anastomosis. In addition to creating a surgical field in which it is difficult to see, leakage of fluid from the anastomosis can cause serious drops in blood pressure, acute or chronic. The loss of blood may cause other deleterious effects on the patient's hemodynamics that may even endanger the patient's life. In addition, blood loss may induce local scar tissue to develop which often results in further blockage within or damage to the sewn vessel. Furthermore, anastomosing blood vessels may involve risks of physical injury to the patient. For example, when performing coronary artery bypass graffing (CABG) procedures, anastomosis often requires manipulation of the heart, so that surgeons may access the back of the heart as well as the front. When done on a beating heart, this manipulation may result in hemodynamic compromise possibly subjecting the patient to cardiac arrest, particularly during lengthy procedures. In "stopped heart" procedures, patients are supported by cardiopulmonary bypass and, thus, risk post-surgical complications (e.g., stroke) that vary directly with the duration for which the heart is under cardioplegic arrest. Consequently, surgeons are constantly searching for techniques to both reduce the risk of tissue damage as well as the laborious and time-consuming task of vessel suturing.

Stapling and coupling procedures have been used in performing large conduit anastomosis. While stapling is successful in gastrointestinal procedures due to the large size and durability of the vessels, as briefly mentioned above, it is less adequate for use in vascular anastomosis. The manufacturing of stapling instruments small enough to be useful for anastomosing smaller vessels, such as coronary arteries, is very difficult and expensive. As stapling instruments are typically made of at least some rigid and fixed components, a stapler of one size will not necessarily work with multiple sizes of vessels. This requires a surgeon to have on hand at least several stapling instruments of varying sizes. This may significantly raise the cost of the equipment and ultimately the cost of the procedure.

When staples are adapted to conform to the smaller sized vessels, they are difficult to maneuver and require a great deal of time, precision, and fine movement to successfully approximate the vessel tissue. Often stapling or coupling devices require the eversion of the vessel walls to provide intima-to-intima contact between the anastomosed vessels. Everting may not always be practical especially for smaller arteries because of the likelihood of tearing when everted. Another factor which may lead to damage or laceration of the vessel and/or leakage at the anastomosis site is the variability of the force that a surgeon may use to fire a stapling instrument causing the possible over- or under-stapling of a vessel. Still other factors include the unintended inversion of the vessel edges and the spacing between staple points. Rectifying a poorly stapled anastomosis is itself a complicated, time-consuming process which can further damage a vessel.

Accordingly, there is a need for an easier, safer and more efficient means for forming anastomotic connections which requires less time and access space than conventional anastomotic procedures.

3. Relevant Literature

U.S. patents of interest include: U.S. Pat. Nos. 6,113,612; 6,113,611; 6,090,136; 6,068,656; 6,068,637; 6,063,114;

6,056,762; 6,036,704; 6,036,703; 6,036,702; 6,030,392; 6,026,814; 6,007,576; 6,007,544; 6,001,123; 5,961,545; 5,948,018; 5,921,995; 5,916,226; 5,904,697; and 4,214,586. Also of interest are the following PCT publications: WO 00/24339; WO 99/65409; WO 99/48427; WO 99/45852; WO 99/08603; WO 98/52474; WO 98/40036; WO 97/31591 and WO 97/31590.

BRIEF DESCRIPTION OF THE DRAWINGS

FIG. 4 includes FIGS. 4A, 4B and 4C all of which show a alternative side-to-side embodiment of the invention with FIG. 4A showing a first segment of the device in a completely folded form being inserted within an opening in a vessel, FIG. 4B showing the first segment partially unfolded and further inserted within the vessel and FIG. 4C showing the first segment completely unfolded and completely inserted within the vessel;

FIG. 5 shows an alternative side-to-side embodiment of the invention where the first and second segments are connected in a manner such that each segment is at a right angle or perpendicular to the other segment;

FIG. 12 includes FIGS. 12A and 12B which show an end-to-side embodiment of the invention.

FIG. 12B is a partial cut-away view of the tubular member of the device operatively positioned within a vessel;

FIG. 13 shows another end-to-side embodiment having a two-piece configuration which pieces are connectable with each other for forming a fluid-tight seal between the segment and the tubular member;

FIG. 14 illustrates another embodiment of a segment of the invention; and

SUMMARY OF THE INVENTION

Figure 1:
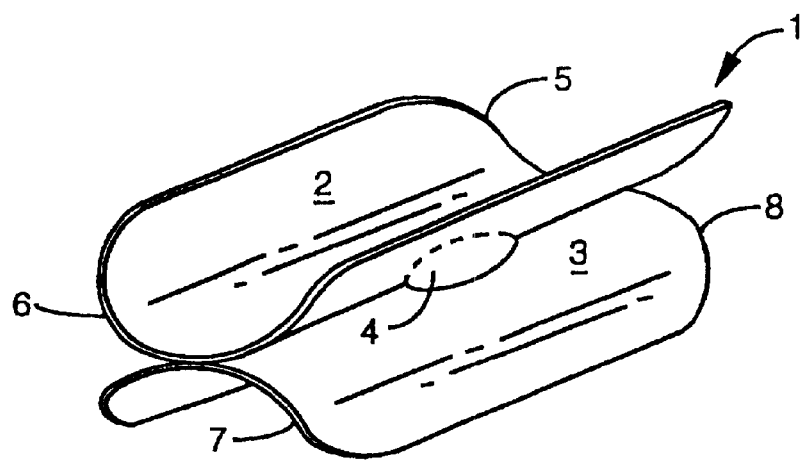
FIG. 1 is a perspective view of a simple side-to-side embodiment of the invention where two partial cylindrical segments are interconnected along the periphery of an opening.

The present invention provides implantable devices and associated methodsfor interconnecting human vessels, lumens, ducts or other tubular organs rapidly, safely and in a minimally invasive manner. These device and methods are particularly helpful in surgical procedures involving small vessels or the like within a limited surgical access field, such as coronary artery bypass graft procedures (CABG). A CABG procedure involves the establishment of an alternate blood supply path to bypass a diseased section of a coronary artery. With the present invention, an implantable device is positioned within a target vessel, such as downstream of a diseased coronary artery, which allows the attachment of a second, graft vessel to form the anastomosis. The procedure for attaching the vessels is called anastomosis.

The subject invention provides devices and methods for forming both side-to-side and end-to-side anastomosis. A side-to-side anastomosis procedure involves the attachment of two vessels at incised locations (e.g., arteriotomies) within a side wall of each of the vessels. An end-to-side anastomosis procedure involves the attachment of two vessels at an incised location within a side wall of one of the vessels and at the transected end of the other vessel.

Common to all of the devices of the present invention is the presence of at least one flexible member, herein also referred to as a first segment in the form of a sheet, membrane or flange. The flexible member is adapted to conform to and seal with an inner surface or circumference of a vessel into which it is delivered. Furthermore, the flexible member is adapted to utilize the internal vessel pressure exerted thereon to form a substantially fluid-tight seal with the inner surface of the conduit whereby substances within the vessel are prevented from leaking from the artificial opening under normal physiological conditions.

More particularly, the flexible member has first and second surfaces. The first surface, herein also referred to as the lumen-facing surface, is adapted to utilize the internal conduit pressure exerted thereon to form a substantially fluid-tight seal between the second surface and an inner surface of the conduit. The second surface, herein also referred to as the contact surface, is adapted to contact and form a substantially fluid-tight seal with an inner wall or circumference of the vessel. Thus, upon deployment of the flexible member into a vessel, the member conforms to the interior walls of the vessel to provide a sealing contact along the second surface and sufficient physical stability to the device to prevent displacement from the vessel. Moreover, the substantially fluid-tight seal is formed without compressing, tensioning or puncturing the vessel wall.

The side-to-side anastomotic devices of the subject invention include both a first segment and a second segment connected by a flow opening along the periphery of the two connected segments. The first and second segments are sufficiently flexible and compliant, as well as sufficiently stiff, for easy insertion into an incision made within each vessel. Upon release, each segment subsequently conforms to the interior walls of a conduit to provide a sealing contact along the contact surface of the segment. Once deployed within the conduits, the sealing contact and stiffness properties of the segments provide sufficient physical stability to the device to prevent displacement from the respective vessels. The flow opening provides a pathway through which fluid can be transported between anastomosed conduits. More specifically, the flow opening provides a location of permanent connection between the two segments of the anastomosis device and, thus, establishes fluid communication between the vessels connected by the implanted device.

The end-to-side anastomotic devices of the subject invention include a first segment as described above positioned at one end of a tubular member, where the tubular member and the first segment are connected by a flow opening analogous to that found in the side-to-side device of the present invention. The first segment of the end-to-side device has the same or similar properties and advantages as described above with respect to the segments of the side-to-side device. The tubular member may be normal to, or positioned at an angle relative to, the surface of the first segment.

The segments of the subject devices constrictable (such as by bending or folding) to a size sufficient to fit through the artificial opening and are expandable to be securely and permanently self-retained within the vessel upon implantation. The segments comprise relatively thin walls, thus minimally interfering with fluid flow within the interconnected vessels. The intravascular pressure against the underside of the segment secures the segment against the inside vessel wall thereby preventing leakage from the anastomosis site. Additionally, the configuration of the segments is such that it provides an element of passive force when deployed within the vessel so as to pull the two vessels together for better sealing and healing of the vessel walls. The selection of materials for making the implantable devices of the present invention is also important for the devices to achieve their intended purposes. In addition to being adequately biocompatible, the material(s) have appropriate mechanical properties for facilitating insertion, retention and sealing of the segments within the vessels. Additionally, the biocompatible devices may be made of any suitable bioresorbable and/or biodegradable materials, as well as autologous, allo- and xeno-graft biomaterials.

The implantable devices of the present invention are preferably in the form of a single-component unit but may be comprised of two (and possibly more) connectable components or pieces. The devices may be inserted or implanted using surgical tools or alternatively using a catheter designed specifically for the less invasive placement and release of the device within the vessels for interconnection thereof. The present invention may be provided in an assortment of sizes, shapes, configurations, etc. in order to interconnect vessels of various sizes, shapes and orientations. Also, the device(s) may be provided as a component of a kit along with other accessory components such as instruments for making an incision or arteriotomy in a vessel to be anastomosed, for sizing or measuring the vessels for determining the proper size of the device to be implanted, for sizing the intravascular segment, and for inserting the device into a vessel. These accessory instruments may perform one or more of the above functions either simultaneously or successively during the procedure. For example, an instrument capable of creating an arteriotomy may also be configured to successively insert an anastomosis device of the present invention into that arteriotomy. Preferably, the successive steps may be accomplished in a singular action or one fluid motion of the instrument.

The implantable devices may be used to join any two (or more) vessels together such that fluid communication is established between the lumens of the two joined vessels, where representative types of vessels include, but are not limited to, vascular vessels and other vessels of the body, where one of the vessels may be a synthetic vessel or graft vessel from a donor, e.g., autograft or allograft. While the specific embodiments described herein illustrate devices for joining only two vessels, those skilled in the art can appreciate that embodiments for joining three, or possibly four or more, vessels are possible under the present invention.

As mentioned above, the implantable device, and the associated implant methods, are particularly applicable for performing anastomosis surgery for grafting two juxtaposed cardiac vessels or for grafting a native vessel to one or more natural or synthetic graft vessels. The CABG surgery may be performed on either a stopped or a beating heart. In many embodiments of interest, the subject devices and methods are employed in distal anastomosis applications, although other anastomosis applications are also of interest, e.g., proximal, etc.

An object of the invention is to provide a device for interconnecting two vessels within a patient—which device is configured so as to be easily inserted into an opening in a vessel and allow for a flow of material through the vessel after insertion.

Another object of the invention is to provide for a method of quickly and efficiently performing an anastomosis.

Another object of the present invention is to provide anastomotic devices and methods which avoid puncturing of a vessel and which avoid or minimize tension and compression forces at the site of the anastomosis.

Another object of the present invention is to provide an anastomotic device whose primary means of sealing to the vessel is by the device's ability to conform to the inside vessel wall and then by the intravascular pressures against the device caused by flow within the vessel.

Yet another object of the present invention is to provide anastomotic devices and methods which minimize the risk of creating emboli while performing an anastomosis procedure.

An advantage of the invention is that the method can be readily performed because the device is small, flexible and easily manipulated.

A feature of the invention is that it can be comprised of a variety of materials.

Another feature of the invention is that the device is flexible and readily conforms to the inside wall of the native vessels to minimize irritation to the endothelial cells of the vessel wall.

Another feature of the device is that the surface contact area of the device to the vessel wall is minimized to reduce unwanted biological responses to the implant.

Another feature of the invention is that one device can be used to accommodate a wide range of different size vessels.

Another feature of the invention is that the device can be sold as a kit containing a range of different sizes of devices that could be useful for insertion into a wider range of vessel sizes.

Another feature of the invention is that the device can be sold as a kit containing the means to size the intravascular segment for insertion into a range of vessel sizes.

Another feature of the invention is that the intraluminal pressure provides a sealing force on the implanted device to prevent leakage at the anastomosis site.

An aspect of the invention is a side-to-side anastomotic device comprised of a first segment connected to a second segment along the periphery of an interconnecting opening.

Another aspect of the invention is an end-to-side anastomotic device comprised of a first segment connected to a tubular member along the periphery of an interconnecting opening.

Another aspect of the invention is that the device can be loaded into a catheter delivery system.

Another aspect of the invention is that the device can be loaded into a surgical delivery dispenser.

Another aspect of the invention is that it facilitates the application of adhesive.

Another aspect of the invention is that it can be inserted using robotic assist devices (U.S. Pat. No. 5,855,583).

Another aspect of the invention is that it can be used with a variety of conduits, vascular grafts, artificial or prosthetic. Examples of vascular grafts are coronary artery to the coronary vein, radial artery to the coronary artery, saphenous vein to the coronary artery, gastroepoploic artery to the coronary arteries, femoro-popletial bypass using vein or other conduit, etc.

Yet another aspect of the invention is that the anastomosis procedure can be carried out using a loading device or an endovascular catheter in order to insert a device of the invention.

These and other objects, aspects, advantages and features of the invention will become apparent to those skilled in the art upon reading this disclosure in combination with the accompanying figures.

DETAILED DESCRIPTION OF THE SPECIFIC EMBODIMENTS

As summarized above, the subject invention provides implantable anastomotic devices and methods for using the same. The subject devices are characterized by having at least one segment, a "first segment," that, upon deployment in a vessel, conforms to the inner surface of the vessel wall in a manner such that a sealing relationship is produced between the implanted device and the vessel wall. This sealing relationship is passive in that no other mechanical (e.g., staples, sutures, etc.) or adhesive (e.g., a biological glue) means is used or is necessary to be used for maintaining the sealed engagement of this first segment. Instead, the sealing engagement is caused primarily by the ability of the device to conform within and to the vessel wall and to be retained in that sealing relationship by means of the pressure within the vessel.

Both side-to-side and end-to-side anastomotic devices are provided by the subject invention. Also provided are kits for use in performing anastomotic procedures, including both side-to-side and end-to-side anastomotic procedures. In further describing the subject invention, the devices themselves are first described in greater detail, followed by a review of various representative anastomotic protocols in which the devices may be employed and a further elaboration on the kits of the subject invention.

Before the present invention, devices and methods used therein are disclosed and described, it is to be understood that this invention is not limited to the particular components, devices or steps illustrated and discussed, as such may, of course, vary. For example, the devices of the invention and use of these devices is primarily described in the context of CABG procedures; however, the invention is useful for many other medical procedures for the connection of other natural and synthetic lumens and organs. Some of these other procedures include general vascular reconstruction and cerebral spinal fluid shunting for the treatment of hydrocephalus. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided are subject to change if it is found that the actual date of publication is different from that provided here.

Anastomotic Devices

As summarized above, the subject anastomotic devices, for both side-to-side and end-to-side applications, are all characterized as having at least one segment (a "first segment") that, upon deployment in a vessel, conforms to the interior walls of the vessel to provide a sealing contact along the contact surface of the segment inserted within the vessel. By "sealing contact" it is meant that the area of contact produces a barrier that is substantially impervious to fluid flow, such that fluid does not flow across the border defined by the area of the contact.

In certain embodiments, at least a portion of the segment is comprised of a flexible, compliant material to enhance conformity of the segment to the vessel wall. The compliant material may take the form of a membrane or flange, or a plurality of membranes or flange elements which can be easily constricted for ease of insertion but which have a natural tendency to return to an unconstricted (i.e., an unfolded or unbent) configuration to readily seal to and conform with the inside vessel wall. In some embodiments, this tendency provides a spring-like force that assists in securing the flanges to the vessel wall. When operatively placed, the membrane(s) or flange(s) are caused to press against at least a portion of the inside wall of the target vessel primarily by the pressure within the target vessel, for example, by the intravascular blood pressure in the context of a CABG procedure. Thus, the contact and conformation of the segment or a flange portion thereof to the vessel wall is accomplished passively, preferably without the additional use of adhesive (e.g., biologic glue) means or means which penetrate and compress the vessel wall (e.g. staples or sutures).

The configuration and dimensions of the flexible segments of the subject devices are important for the devices to accomplish their intended purposes. More specifically, each segment has a thickness(es), surface area, length and width (or diameter) dimensions for optimizing insertability of the segment into the vessel, maximizing the sealability of the segment to the vessel wall, minimally interfering with fluid flow within the interconnected vessels and maximizing the tensile strength of the device to retain itself (i.e., "self-retaining") within the vessel under a range of likely physiological conditions without the need for an ancillary fixation or retention device or component.

The segments comprise relatively thin-walls, thus minimally interfering with fluid flow within the interconnected vessels. A segment may have one continuous thickness or may have varying thicknesses throughout its structure. In either case, the segments have optimal thicknesses such that segments are sufficiently compliant and flexible so as to be compressible for insertion into a vessel, while being sufficiently rigid to facilitate insertion without the segment folding on itself or becoming kinked or otherwise mechanically damaged upon entry into the vessel.

The thickness as well as the surface area of a segment are also optimized for providing sufficient physical stability so that the segment remains securely positioned within the vessel particularly when subject to internal forces (e.g., an increase in a patient's blood pressure either during or after surgery) and/or external forces (e.g., the tugging and pulling that are likely to result from manipulation of the device during the anastomosis procedure or by the normal beating of the patient's heart after the procedure).

Still further, the thickness and surface area of the segments are such that, when operatively used, cause the segment(s) to provide an element of passive force that can pull the two anastomized vessels together. More specifically, the pressure against the wall created by the intravascular fluid flow or blood pressure, which is typically in the range from about 60 to 180 mm of Hg under normal conditions, secures each segment in a sealing engagement against the inside vessel wall. This sealing engagement holds the individual segments in a stable and permanent position within the vessel. The sealing engagement also prevents the leakage of fluid from the incision or arteriotomy within the vessel wall during the implantation of the device, as well as from the resulting anastomotic site after completion of the anastomosis procedure. The stable and leak-free positioning of the device enables the vessels, and more particularly their respective incised edges, to be accurately appositioned with respect to each other, thereby facilitating the natural tissue bonding between the two, preferably without the use or with minimal use of other mechanical or adhesive means.

Figure 9:
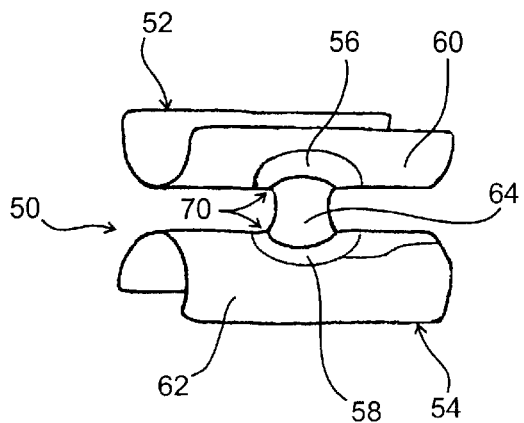
FIG. 9 illustrates another side-to-side embodiment of the invention having a flow channel extending between the two segments.

As described below in greater detail, the segments of the present invention may have a variety of different configurations, thickness(es), surface areas, lengths and widths (or diameters). For example, useful configurations include, but are not limited to, partial (see FIGS. 1, 2, 5, 7A–E, 9 and 10) and full cylinders (see FIG. 3), or generally planar configurations having circular (see FIGS. 6A–C and 11A–B), elliptical (see FIGS. 12A and 15A–C), stared, pedaled or rectangular shapes, or combinations of these configurations (e.g., see FIG. 9 showing a segment having a generally planar rectangular shape which is conformable into a partial cylinder). Generally, the size and shape of the segments of the present invention are dependent on the size (i.e., the circumference or diameter) and shape of the bodily lumen into which it is to be used. For example, larger segments may be preferable when performing a proximal anastomosis to an aorta, or when anastomosing peripheral (e.g., in the leg) or abdominal vessels while smaller segments are more appropriate for coronary arteries and veins. Also, the length or width (or diameter) dimensions or both, may be dictated by the length of the incision or arteriotomy within the lumen or vessel into which the segment is to be placed.

In side-to-side embodiments of the device, the flow opening between the segments which establishes fluid communication between the two may also have varying shapes and sizes according to the size of the arteriotomy and the application in which it is being used. The length of the flow opening (i.e., the distance between the two segments), may also vary depending on the distance between the vessels' respective attachment points. In some embodiments, where the outer surfaces of the segments are close enough to touch each other, the flow opening for each of the segments is necessarily one and the same (see FIGS. 1, 3, 4A–C, 5, 6A–C and 7A–E). Other embodiments have flow openings that define a tubular pathway or channel between the segments (see FIGS. 9, 10 and 11A–B). The flow opening between segments is configured to minimize disturbances to the fluid flow such as turbulence or no-flow regions.

Both side-to-side and end-to-side anastomotic devices are provided by the subject invention and are now separately described in greater detail below.

Side-to-Side Anastomotic Devices

The side-to-side anastomotic devices of the subject invention include a first segment and a second segment connected by a flow opening along the periphery of the two connected segments or by a flow channel extending between the respective flow openings. The first and second segments are flexible and compliant for easy insertion into an incision made within each vessel. Upon release, each segment subsequently conforms to the interior walls of a vessel to provide a sealing contact along the contact surface of the segment inserted within the vessel. Preferably, the features mentioned above with respect to the first segment also apply to the second segment of the side-to-side embodiments of the present invention. The flow opening/channel provides a permanent connection between the two segments and fluid communication between the vessels connected by the implanted device.

FIG. 1 shows the flexible device 1 that is comprised of a first segment 2 and a second segment 3. In this embodiment the first segment 2 and the second segment 3 are mirror images of each other and are interconnected (preferably in a permanent manner) to each other along the periphery of an interconnecting opening 4. The first segment 2 has an end 5 and an opposite end 6. The ends 5 and 6 are equal distance from the center of the opening 4. Although the ends shown here have smooth, rounded edges the ends may be shaped in any desired form noting that it is preferable to have end edges which can be easily inserted into a vessel and not cause damage to the vessel. The second segment 3 has an end 7 and an opposite end 8 each of which are also equal distance from the center of the opening 4. In their unconstricted, unfolded or unbent states, segments 2 and 3 each have a generally planar configuration but may, however, have other than planar configurations (e.g., cylindrical) in an unconstricted state.

Figure 2:
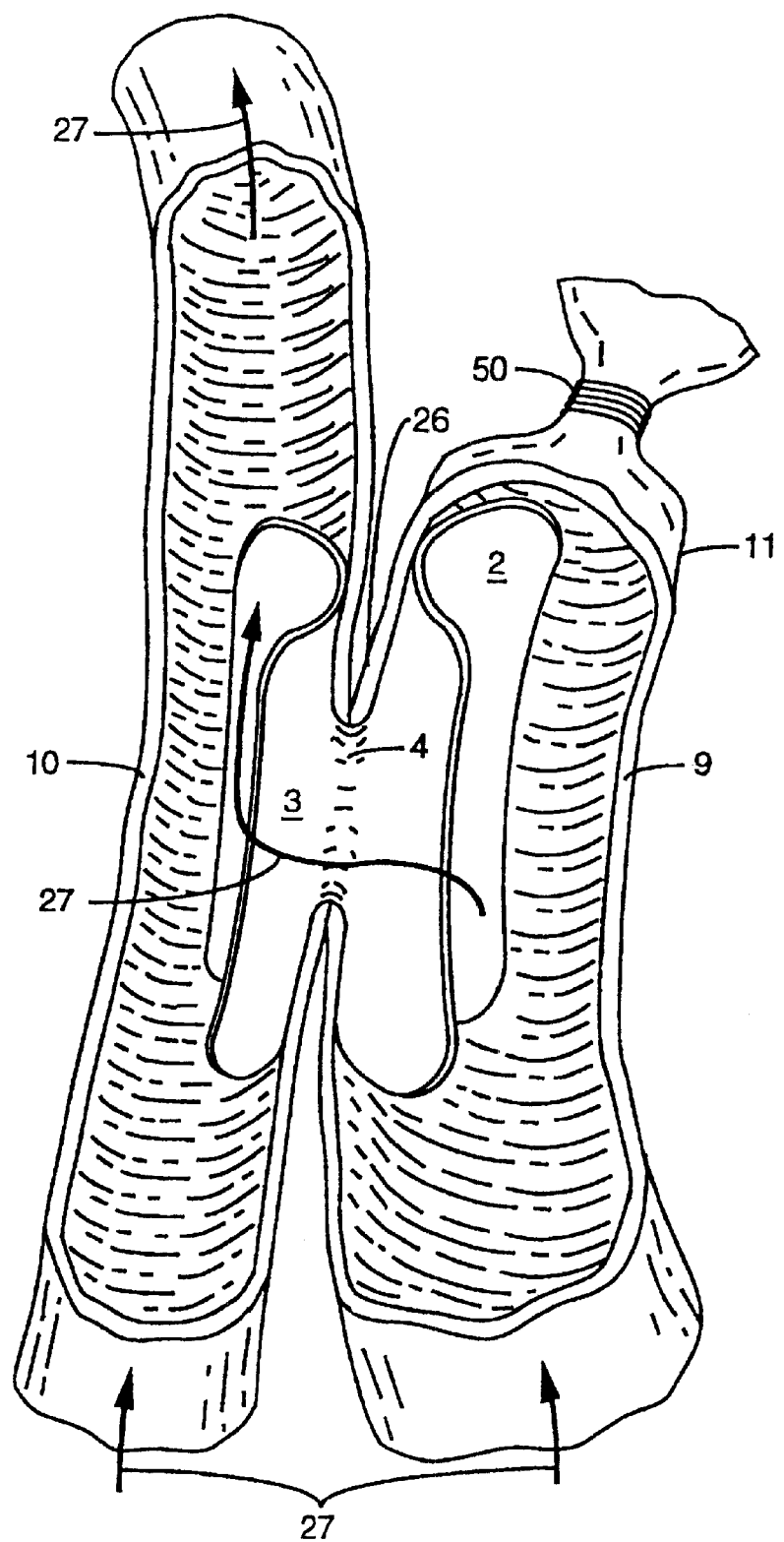
FIG. 2 shows the embodiment of FIG. 1 inserted within two vessels thereby interconnecting those vessels.

The device 1 as shown in FIG. 1 is shown inserted into vessels 9 and 10 in FIG. 2. Depending on the particular configuration of the device 1 the insertion can be carried out in a number of different ways. As an example, the first segment 2 can be constricted, either manually or by the aid of an insertion tool, so that it forms a tighter semi-circle and/or the ends 5 and 6 can be folded towards each other. In this position the ends 5 and 6 can be made to touch each other and can be inserted within the opening of a first vessel 9. Thereafter the second segment 3 can be inserted within an opening of a second vessel 10 in the same manner. Once properly seated within the vessel, each segment is released from its constricted state and allowed to deploy whereby the respective ends unfold or expand and move against and conform to the inside vessel wall thereby establishing a fluid pathway between the vessels via the center of opening 4. Thus, a side-to-side interconnection of vessels 9 and 10 is completed. In many situations it is desirable to close off one end of one of the vessels. As shown in FIG. 2, the end 11 of the vessel 9 has been tied off.

In the embodiment of the device 1 as shown in FIG. 1 the first segment 2 and second segment 3 are mirror images. However, the two segments can be different in size (circumference, width or length) and shape from each other. Different sizes are useful in situations where it is desirable to interconnect two vessels which are different in size. The embodiment of FIG. 1 also shows that the ends 5 and 6 of the first segment 2 as well as the ends 7 and 8 of the second segment 3 are equal distance along their entire edge from the center of the opening 4. However, the ends 5, 6, 7 and 8 can be configured in any given manner and distance from interconnection hole 4 as well as being tapered or rounded on each or either end.

FIG. 2 illustrates an exemplary anastomosis surgery consisting of grafting two juxtaposed vessels 9 and 10. After creating an artificial opening (e.g., an arteriotomy) in each vessel, the surgeon inserts one segment 2 in one vessel 9 and the other segment 3 into the other vessel 10 whereby the pressure created by device 1 due to expansion of its segments and the action of intraluminal pressure prevents leakage of fluid from the graft site 26. The fluid then passes along flow path 27 from vessel 9 through the hollow connecting hole 4 into the vessel 10. The surgeon may tie off the distal end of the graft vessel using a thread 50, staple or other suitable closure or binding means. When the segments 2, 3 expand back to their original size and shape, they will conform to the vessel walls to provide a sealing pressure and a firm fit.

After insertion and completion of the anastomosis using the device 1 shown in FIG. 1 and inserted within the vessels of FIG. 2, it is necessary that the free end of the vessel be tied off by any standard closure or binding means using sutures, metal clips or other securing mechanisms such as the thread 50 shown in FIG. 2. For example, the saphenous vein, right or left internal mammary artery, or radial artery used to form the anastomosis is terminated or closed off at the end as shown with the thread 50. Other closure means are taught in U.S. Pat. No. 5,234,448. Closing off of the vessel 9 would clearly not be necessary during any side-to-side anastomosis where the vessel is to be anastomosed to another vessel at a more distant point. During the procedure, the placement of one to three stay sutures in order to stabilize the graft to the heart or to juxtaposition the two vessels together may be desired. Such sutures are easily placed through the fat or tissue surrounding the vessels in order to provide additional stability to the anastomosis. This is normally performed when grafting an internal mammary artery to the coronaries but may be required during implantation of the inventive device in order to prevent the anastomosed vessels from being inadvertently separated from each other during or after the procedure. However, far fewer, if any at all, suture points would be required or used in the context of the methods of the present invention than would otherwise be used in the case where an entire anastomosis is formed by suturing alone.

Although the device 1 shows a first segment 2 and second segment 3 each of which has a partial cylindrical shape and each of which is identical in size and shape to the other, a variety of different configurations are contemplated by the present invention. Some of these configurations are shown in the other embodiments—see FIGS. 3, 4, 5, 6, 9, 10, 11 and 12. However, those skilled in the art will contemplate numerous additional embodiments upon reading this disclosure. As one example it is pointed out that the first segment 2 and second segment 3 can be generally flat or planar, i.e., have outer surfaces which are contained within a single plane. If each segment is flat or generally planar, then the segment is folded before being placed in the opening of a vessel. Once in place each segment will assume the configuration of the interior wall of the vessel it is placed within. Further, each segment will apply some pressure against the interior wall of the vessel thereby holding the device in place. With each of the embodiments of the invention, the segments may be designed to be flexible and in a slightly bent or constricted shape when present within the interior wall of the vessel so that the outer surface of each segment is forcing itself against the interior wall of the vessel while the device is attempting to reassume its original configuration. This aspect of the devices augments the force created by blood pressure or other fluid pressure within the vessels that holds the device in place.

In the device 1 shown in FIG. 1 and used within FIG. 2, the first segment 2 and second segment 3 are connected along the periphery of the opening 4. Accordingly, the first segment 2 and second segment 3 touch each other along a line extending outwardly along the periphery of the opening 4 to the respective ends of each segment. However, in alternative embodiments, the opening 4 can be in the form of an open channel that could be cylindrical in shape (see FIG. 9, for example). The open channel would connect to the opening 4 on each segment of the device. The channel would separate the first segment 2 from the second segment 3 by the length of the channel and it would be used in situations where the vessels being connected are not positionable against each other. For example, one of the vessels may be embedded within a layer of muscle or other tissue.

Figure 3:
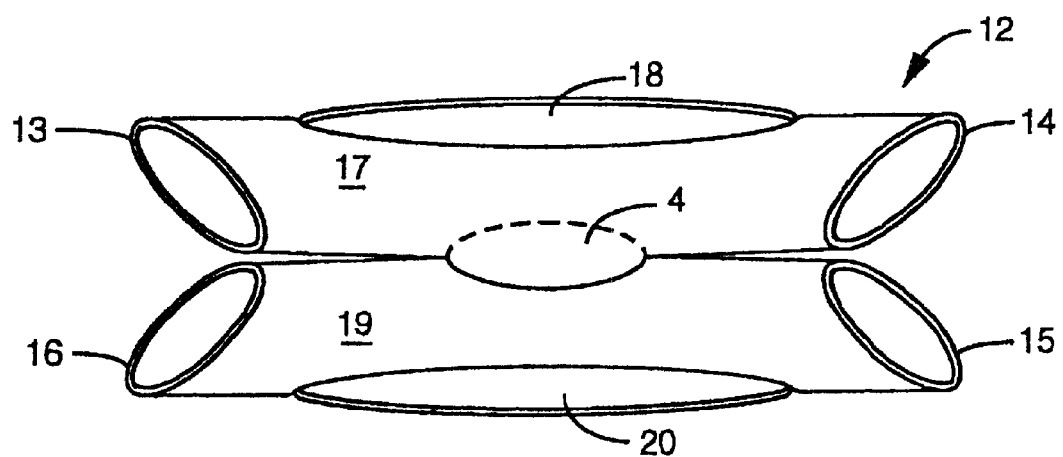
FIG. 3 shows an alternative side-to-side embodiment of the device of the invention where full (complete) cylindrical segments having tapered ends are interconnected along the periphery of an opening wherein each of the segments has an opening in its upper surface.

FIG. 3 shows an alternative embodiment 12 of the invented device having tubular segments 17 and 19. Tubular segment 17 comprises tapered ends 13 and 14 and tubular segment 19 comprises tapered ends 15 and 16. The tapering of these ends may have a low friction coating and be very smooth thereby providing a number of advantages which include making it easier to insert into a vessel. The configuration of FIG. 1 shows that the first segment and second segment are each configured in the form of a portion of a cylinder in an unconstricted state. However, the device could be configured so that each segment is a complete cylinder (see FIG. 3) in an unconstricted or constricted state. An advantage of having each of the segments a partial cylinder is the ability to conform to a wider range of different vessel diameters to improve the fitting range. Another advantage is the maximizing of the amount of endothelial wall of the vessel not covered by the device 12 to minimize any negative biological response to the implantable device 12. In the configuration shown in FIG. 3 a complete cylinder is provided for each segment. However, the first segment 17 has an opening 18 in its upper surface and the second segment 19 has an opening 20 in its upper surface.

Another embodiment of the invention is shown in FIGS. 4A, 4B and 4C each of which shows a folding/expandable device 21. In FIG. 4A the segment 22 is in its expanded configuration and the segment 23 is in a completely folded configuration. FIG. 4A shows the segment 23 being inserted into an opening 24 in a vessel 25. Once the segment 23 has been inserted, it is released and it begins expanding to a partially folded configuration as shown in FIG. 4B. FIG. 4C shows the segment 23 completely expanded. After this procedure is completed the same procedure could be carried out with the segment 22 on a separate vessel (not shown).

In device 1 of FIG. 1, the first segment 2 and the second segment 3 are connected in a manner such that they are parallel to each other. However, as shown in FIG. 5 the first segment 30 may be positioned at a right angle to the second segment 31. As with the embodiment as shown in FIG. 1 the device 33 shown in FIG. 5 has the segments 30 and 31 interconnected along the periphery of an opening 4. Those skilled in the art will recognize that the segments of the device can be interconnected at other places. However, interconnection in some manner along or near the periphery of the opening is important in order to provide a seal between the first and second segments. The device 33 shown in FIG. 5 is also different from the device 1 shown in FIG. 1 in that the first segment 30 is larger in diameter than the second segment 31. This differentiation in the diameter of the two segments is preferable in situations where the surgeon is interconnecting two vessels which are different in diameter.

In the embodiment as shown in FIG. 5 the first segment 30 and second segment 31 are positioned at a 90° angle with respect to each other. However, the first and second segments can be positioned at any angle relative to each other, i.e., any angle between being directly parallel as shown in FIG. 1 to being at a right angle or 90° angle as shown in FIG. 5. Thus, the embodiment of FIG. 1 shows the first segment 2 and second segment 3 positioned at a 0° angle. In this position it is sometimes difficult to provide the necessary access in terms of a required line of sight or manual manipulations. Accordingly, offsetting one segment relative to the other at some angle (between 0° to 90° or more preferably between 20° to 90°) may improve visual and manual access. In the embodiment of FIG. 5 the first segment 30 and second segment 31 are directly connected to each other along the periphery of the flow opening 4. However, as explained above, the first and second segments may be interconnected by a channel. The channel could be of any length but is preferably 2 cm or less in length and has a diameter which is substantially equal to the diameter of the interior wall of one or both of the vessels being connected, and, as such, is designed to minimize flow disturbances.

The device 33 shown in FIG. 5 is also different from the prior configuration shown in FIG. 1 in another important feature. Specifically, the larger first tubular segment 30 nearly forms a complete cylinder. The edges 34 and 35 are close to each other compared to those of the device shown in the configuration of FIG. 1, which forms half or less than half of a cylinder. The second tubular segment 31 (FIG. 5) is shown in a state where it initially forms a complete cylinder along a separation string or thread 37 (shown along the dashed line 36). When thread 37 is pulled the edges of the second tubular segment 31 separate causing the tubular segment to form a partial cylinder as is shown with the first tubular segment 30. Thus, the second tubular segment 31 is shown in its original state wherein the first tubular segment 30 is shown in a state after the separation thread 37 has been pulled apart. Once the separation thread 37 has been pulled apart and the edges are separated from each other, the cylinder expands radially outwardly to conform to the interior walls of the vessel. Thus, the device is first inserted into the vessels and then the separation thread 37 in each tubular segment is pulled apart allowing the edges to separate and the partial cylinder to expand and apply force against the interior walls of the vessel. In this manner the device is securely held in place and the fluid flow within the vessel is not obstructed by the device.

In describing the device of the present invention the terminology "conforms" or "conforms to" and the like is used to refer to the outer surface area of each segment of the device. What is intended by this terminology is that the device is designed to sufficiently conform and seal the interior walls of the vessel when it is placed within. As indicated above each segment of the device may be planar in configuration and bent into a curved cylindrical portion during insertion into a vessel. Once the segment is inserted and released, the segment attempts to resume its original configuration, with the additional action of intraluminal pressure, it conforms substantially to the interior walls of the vessel.

The embodiment shown in FIG. 5 shows the application of a thread 37 for separating the edges of a tubular segment and conforming to the interior walls of the vessel. Other means for edge separation and constriction are possible for use with the present invention. For example, both segments or portions of the device shown in FIG. 5 could be separated providing edges such as the edges 34 and 35 shown in the first segment 30. A thread could be tied around the first segment 30 forcing the edges 34 and 35 together or even forcing them to overlap each other. Thereafter the segment 30 is placed within the vessel and the thread is removed. After the thread is removed the segment 30 attempts to resume its original configuration and the outer surfaces of the segment 30 force themselves against the inner surfaces of the vessel and thereby conform to the interior wall of the vessel. Other means of constricting the diameter of each segment or portion prior to insertion and thereafter allowing that segment or portion to relax and attempt to reassume its original configuration are contemplated by the present invention.

FIG. 9 illustrates yet another embodiment of a side-to-side device 50 of the subject invention. Device 50 has a first segment 52 and a second segment 54, each having a rectangular contact surface which, when in constricted conditions, have a semi-cylindrical configuration. Segments 52, 54 each comprise a reinforcement portion 56 and 58, respectively, and a membrane or flange portion 60 and 62, respectively. Within the boundaries of the reinforcement portions 56, 58 are flow openings in between which extends a flow channel 64 providing fluid communication between the vessels into which the segments 52, 54 are inserted. Reinforcement portions 56 and 58 are integral with flange portions 60 and 62, respectively, and act to further reinforce the sealing force of the flanges against the vessel walls. Here, reinforcement portions 56, 58 have a circular configuration comprising a surface area which extends radially outward from their respective flow openings. However, reinforcement portions 56, 58 may have any other appropriate configuration including, but not limited to, a ridge, radially extending petals, an ellipse or a rectangle. The respective flange portions 60, 62 are made of the of the same or similar materials as the segments of the embodiments described. Furthermore, flange portions 60, 62 may have the same or similar biocompatibility, sealing, insertion, compliance and tensile properties as the segments of the embodiments described above. Reinforcement portions 56, 58 are preferably incorporate a polymer material such as nylon, polypropylene, and polyethylene, or a metal such as stainless steel or nitinol. To provide a ridge configuration, the material may be in the form of a monofilament. The reinforcement acts to better support and stabilize the segments 52, 54, respectively, within the vessels into which they are implanted, and thus, optimizing the overall stability of the device, once the anastomosis has been completed.

Although FIG. 9 illustrates base portions 56, 58 as having annular configurations that encircle the circumference of the respective flow openings, the reinforcement portions may have any appropriate configuration. For example, the reinforcement portion may also comprise a spine (not shown) that extends radially, in proximal and distal directions, from the flow opening along a line that bisects and is parallel to the longitudinal axis of the segment. Such a configuration facilitates the folding or constricting of the flange portions and provides additional stiffness to the segment as it is being inserted into a vessel.

Another aspect of the devices of the present invention that is important to consider is the radius of curvature of the juncture between a segment and the flow channel of a device of the present invention. This juncture runs the circumference of the contact area between the segment and the flow channel. The radius of curvature of the junction is selected to minimize turbulence of the fluid flow from the host vessel into the flow channel and from the flow channel into the graft vessel. Additionally, the radius of curvature may be selected to optimize the appositioning of the two vessels. In side-to-side embodiments having a flow channel extending between the segments, there are two such junctures, one between each of the segments and the flow channel. In FIG. 9, these junctures are identified by reference number 70.

Figure 10:
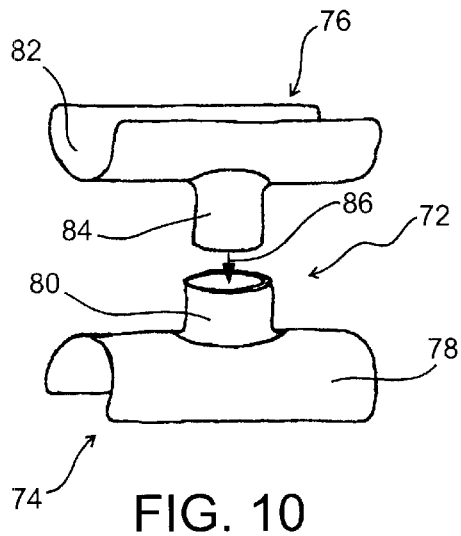
FIG. 10 illustrates another side-to-side embodiment of the invention having a two-piece configuration which pieces are connectable with each other for forming a fluid-tight flow channel between the two segments.

While only single-piece anastomosis devices have been discussed thus far, the present invention also provides for multiple piece devices. For example, FIG. 10 illustrates a side-to-side embodiment of a two-piece device 72 comprising a first piece 74 and a second piece 76. First piece 74 includes a first segment 78 and a first tubular flow channel portion 80 extending substantially perpendicular from the center of first segment 78. Second piece 76 includes a second segment 82 and a second tubular flow channel portion 84 extending substantially perpendicular from the center of second segment 82. First channel portion 80 has an inside diameter substantially the same as the outer diameter of second channel portion 84 such that a fluid-tight flow channel is created when second channel portion 84 is inserted, in the direction of arrow 86, within the lumen of first channel portion 80.

Figure 11A:
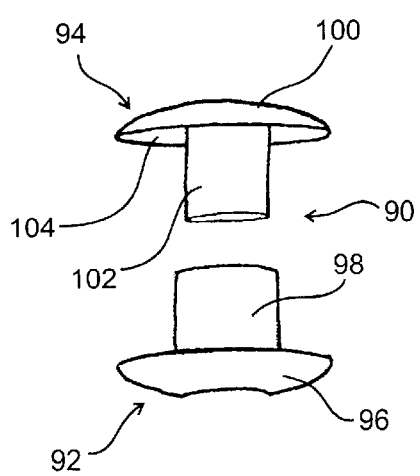
FIG. 11 includes FIGS. 11A and 11B which illustrate yet another side-to-side embodiment of the invention having segments with a rivet-type configuration.
FIG. 11B shows the device having one of its segments operatively positioned within a vessel.
Figure 11B:
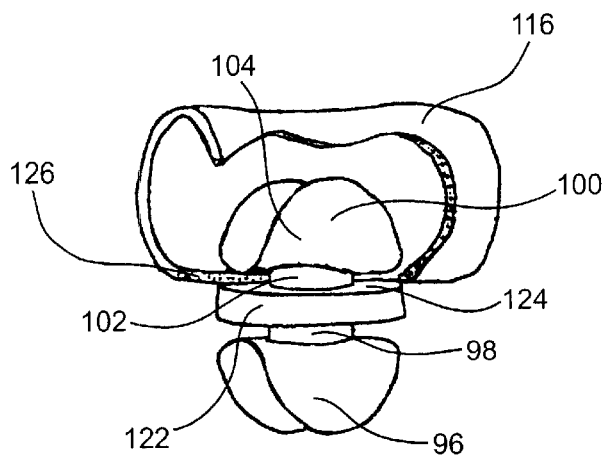

Another two-piece anastomotic device 90 of the present invention is shown in FIGS. 11A and 11B. Device 90 includes a first piece 92 and a second piece 94 each of which has a rivet-like configuration. First piece 92 includes a first segment 96 and a first tubular flow channel portion 98 extending substantially perpendicular from the center of first segment 96. Second piece 94 includes a second segment 100 and a second tubular flow channel portion 102 having the same relative relationship as the corresponding counterparts of first piece 92. First and second channel portions 98 and 102 also have the same relative relationship as their counterparts in FIG. 10 to form a complete flow channel. Here, however, the diameter of the resulting flow channel is greater than that of FIG. 10 and, thus, is more appropriate for use with larger vessels. Also different, is the annular, rivet-like shape of segments 96 and 100 which, when in their natural, unconstricted state (as in FIG. 11A), first and second segments 92, 94 have a cup-like configuration having opposing concave and convex sides. Concaveside 104 of second segment 94, for example, faces the flow channel and opposing first segment 92. However, when operatively placed in a vessel, as shown in FIG. 11B, segments 96, 100 are forced to evert by an inherent spring-force inherent in the design of the device, with the originally concave sides 104 having a contact area flush with the inside of the vessel walls 116, creating a sealing pressure against the vessel walls. The sealing pressure caused by the spring-like action of the implanted segment 100 may be further augmented by a coupling mechanism 122, as shown in FIG. 11B. Here, the two pieces 92 and 94 of device 90 are operatively coupled to each other wherein first flow channel portion 98 of first piece 92 and a second flow channel portion 102 of second piece 94 are in a fluid-tight engagement in the same or similar manner as the device of FIG. 10.

As discussed previously, the primary and secondary means of sealing the segments or flanges of the present invention to the vessel wall are, respectively, the intravascular pressures against the segments or flanges and the physical properties of the segments or flanges themselves (including the reinforcement portion if used, such as reinforcement portions 56 and 58 of FIG. 9). The invention also provides a third and optional means of sealing in the form of a securement member or members which is/are generally positioned proximate the flow channel and/or the junction between the flow channel and which may be internal or external to the device. In FIG. 11B, for example, the securement means is in the form of a single collar, cuff or ring 122. Collar 122 is positioned around the outside of the flow channel and has a thickness such that its end surfaces 124 are in sealing engagement with the outside walls of the interconnected vessels (only one vessel 116 is shown). As such, the vessel wall 126 is atraumatically held between segment 94 and collar 122 with collar 122 acting as an external, static counter force to the internal forces of the segment's natural spring action and of the intravascular pressures. Preferably, at least the end surfaces of collar 122 are made of or coated with a material that stimulates hemostasis and wound healing.

While a number of different configurations are possible, as demonstrated above by the review of various representative configurations, the thickness and the area of contact between the deployed first and second segments and their representative vessels should be sufficient to provide for a sealing contact of sufficient strength to achieve the purpose of the devices. The segments have a surface contact area at least marginally greater than the surface area of the opening in the vessel through with the segment is inserted. For example, for devices suitable for use in CABG anastomosis procedures, the contact surface of the first and second segments has a surface area that is generally in the range from at least about 40 mm$^2$, usually at least about 70 mm$^2$ and more usually at least about 90 mm$^2$, and usually no greater than about 450 mm$^2$ (such as for use in the aorta or other large lumen). The thickness of the first and second segments is generally in the range from about 100 to 500 microns and preferably in the range from about 200 to 400 microns. Exemplary width and length (or diameter) dimensions for these surface area ranges are generally from about 5 to 15 mm for the width and from about 8 to 30 mm for the length. And more usually from about 7 to 9 mm for the width and from about 13 to 15 mm for the length, depending on the exact size of the target vessel to be anastomosed.

In addition, the flow opening has a diameter that provides for the desired flow rate between the two vessels connected by the device. The diameter of the flow opening (and connecting tube depending the particular embodiment) generally approximates the diameter of at least one of the vessels being joined by the device. As such, the diameter of the flow opening is typically at least about 1 mm, usually at least about 2 mm and more usually at least about 3 mm, where the flow channel may be as long as 10 mm or longer, but generally does not exceed about 5 mm and usually does not exceed about 4 mm. In addition, the flow opening may be in the form of an ellipse whose short axis conforms to the specifications for the diameter and whose long axis is typically at least about 1 mm, usually at least about 2 mm and more usually at least about 3 mm, where the long axis may be as long as 5 mm or longer, but generally does not exceed 20 mm.

End-to-Side Anastomotic Devices

The end-to-side anastomotic devices of the present invention, like the side-to-side anastomotic devices of the present invention, are characterized by the presence of a first segment that, upon deployment, forms a sealing relationship with the inner surface of the vessel in which it is deployed. Connected to this first segment at a flow opening is a tubular member, which member is designed to be positioned within the transected end of a graft vessel to be joined to the side of a host vessel.

Referring now to FIGS. 12A–B, 13, 14 and 15A–C, there are illustrated end-to-side anastomotic device embodiments according to the present invention. The one-piece device 130 of FIG. 12A is made up of first segment 134 and a tubular member 140 joined together at flow opening defined externally by juncture 138. First segment 134 is shown as a partial cylinder having an elliptically shaped contact surface. As with the side-to-side embodiments discussed previously, first segment 134 may have any other appropriate shape (e.g., circular, elliptical, rectangular, etc.) and configuration (e.g., a full cylinder, etc.). First segment 134 has a flange section 132 and a reinforcement portions in the form of annular ridge 136 which functions similarly to the reinforcement portions of device 50 of FIG. 9. The length, width, thickness and surface area dimensions of segment 134 are within the ranges provided above with respect to the first and second segments of the side-to-side embodiments.

Tubular member 140 of device 130 extends from the flow opening (not shown) of segment 134 and is designed to fit inside of the transected end of a graft vessel that is to be joined to the side of a host vessel. The length of tubular member 140 typically ranges from about 10 to 20 mm. The outer diameter of tubular member 140 has a dimension that approximates the inner diameter of the graft vessel to be attached, and therefore is typically in the range from about 2 to 6 mm, and more typically from about 3 to 5 mm. The inner diameter of tubular member typically ranges from about 1 to 5 mm, and more typically from about 2 to 4 mm. Also identified in FIG. 12A is juncture 138 at the connecting point between tubular member 140 and first segment 134 which, internal to device 130, defines the flow opening which typically has a diameter that is substantially the same as the inner diameter of the tubular member.

Tubular member 140 has distal end 144 having a vessel securement means 142. Here, vessel securement means is in the form of two parallel rings surrounding the circumference of tubular member 140. After tubular member 140 has been inserted into the graft vessel 149, as illustrated in FIG. 12B, and appropriately positioned vis-á-vis the host vessel (not shown), another component of the securement means, here in the form of a suture, cuff or ring 146 may be temporarily or permanently positioned about the graft vessel 149 and within the spacing formed by rings 142.

Figure 15A:
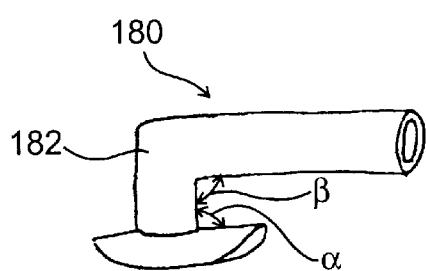
FIG. 15 includes FIGS. 15A, 15B and 15C which illustrate various exemplary end-to-side embodiments of the invention wherein the respective tubular members have varying configurations and are at varying angles to their respective segments.
Figure 15B:
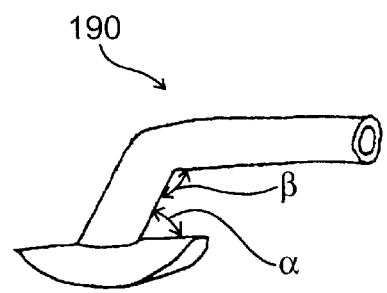
Figure 15C:
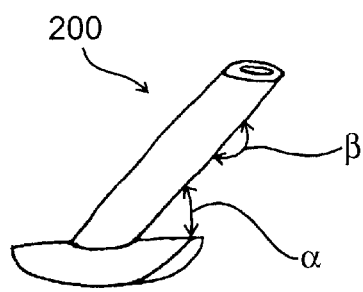

The positioning of tubular member 140 with respect to segment 134 and also the configuration of tubular member 140 may be selected in order to better present tubular member 140 within the surgical field and to facilitate visual and manual access by the surgeon particularly in a minimally invasive opening. For example, tubular member 140 may be angled with respect to first segment 134. While device 130 of FIG. 12A is depicted as having tubular element 140 normal to the upper surface of first segment 134 such that angle α is approximately 90°, tubular element 140 may also be non-normally angled with respect to the upper surface of first segment 134, depending on the particular anastomotic protocol in which the device is to be employed. As such, angle cc may range from about 1° to 90°, and will typically range from about 5° to 90°, and will more usually range from about 20° to 90°. For example, FIGS. 15A–C illustrate exemplary configurations of angle α wherein the device 180 of FIG. 15A has an angle α of 90°, device 190 of FIG. 15B has an angle α approximately between about 50° to 60°, and device 200 of FIG. 15C has an angle α approximately between about 30° to 45°.

The configuration of the tubular member may also facilitate presentation, access and positioning of the vessels being anastomized. Referring again to FIG. 12A, distal end 144 of tubular member 140 is curved but may have any appropriate configuration. For example, tubular member may have a bend or an elbow portion along its length defining an angle β is in the range from about 90° to 179°. Referring now FIGS. 15A–C, tubular member 180 of FIG. 15A has an angle β of about 90°. Tubular member 190 of FIG. 15B has an angle β at about 120°, while angle β of tubular member 200 of FIG. 15C is 180°, having a straight configuration. When operatively positioned, these tubular member configurations may also facilitate positioning of the graft vessel with respect to the native vessel such that the interconnected vessels lie relative to each other in a manner that minimizes any pulling tension that may occur from the natural beating of the heart. Depending on the particular anastomotic protocol in which the device is to be employed, angle β may range from about 90° to 180°. Furthermore, the values of angles α and β can be chose such that the combination of the two optimizes the particular anastomotic procedure at hand.

Referring now to FIG. 13, there is shown a two-piece embodiment of an end-to-side device 150 which has the same general construct as device 130 of FIG. 12A. Here, however, tubular member 158 is a separate component from component 154 which includes a first segment 152 and a first fluid channel portion 156 extending from the flow opening (not shown) of segment 152. The coupling of tubular member 158 to fluid channel portion 156 is accomplished much in the same way that first piece 74 and second piece 76 of FIG. 10 are coupled together.

FIG. 14 shows a side view of an alternate embodiment of a first segment 170 of the present invention having a pleat 172, running centrally along the longitudinal axis of segment 170 to assist folding and deployment of segment 170 within a target vessel.

Materials

The subject anastomotic devices and their components described above maybe fabricated from a variety of different materials. The materials are generally biocompatible by which is meant that they are acceptable for implantation in the body and any adverse bodily reaction to their presence, if any, is not so great as to outweigh the benefit of the device when employed for its intended use. In certain embodiments, the devices are made from a biodegradeable or bioresorbable material, where the terms biodegradeable and bioresorbable are used interchangeably in this specification. Bioresorbable materials of interest include, but are not limited to, degradable hydrogels, polymers such as lactides/glycolides or PHAs; protein cell matrices, plant, carbohydrate derivatives (sugars), and the like. A metal mesh with the appropriate geometrical features, sinusoidal and circular, and cross patterns to provide adequate flexibility may be appropriate in certain circumstances; nitinol (a super elastic nickel titanium alloy) or other shape memory materials or stainless steel can be used. Non-resorbable polymers and elastomers such as silicones, fluoropolymers, polyolephins or polyurethanes might also be used. In addition, the subject devices can be fabricated from composites of two or more different types of materials, etc, e.g., the device may be fabricated from a blood impermeable membrane attached to a structural article or scaffold.

Those skilled in the art will recognize that certain materials are preferred in connection with certain uses of the invention. In general the material should be comprised of one or more materials which are biocompatible and non-toxic to the vessels into which they are inserted. In general the device is used for connecting vessels of the cardiovascular system and therefore should be comprised of a material which provides a high degree of hemocompatibility. The material should not prevent growth of a new intima layer. The material used in the construction of the invented device should be designed to have thickness and properties appropriate for the stiffness and flexibility of the vessel into which the device is inserted. It should be noted that artery walls continuously dilate and contract due to the systole and diastole of the heart. If the device is too rigid the device can cause irritation and injury to the intima layer of the vessel. Accordingly, the device should be designed to avoid any inflammatory response or immune response that has adverse consequences. In addition to having the desired degree of flexibility and composition the device should be designed so that it does not present protrusions or disruptions to the flow of material through the vessels which are being connected by the device. Interruption of flow can cause clots to form which could in certain circumstances be fatal to the patient.

In a preferred embodiment the device of the invention is bioresorbable material and it may be comprised of all or any of the following materials: Collagen, Polycaprolactone, Poly (glycolic acid), PLLA, Poly(3-hydroxybutric acid), Poly(dl-lactic acid), Poly(1-lactic acid), Poly(lactide/glycolide) copolymers, Poly(hydroxyvalerate), Poly(hydroxyvarelate-co-hydroxybutyrate), or other PHAs, or other resorbable materials, e.g., protein cell matrices, plant, carbohydrate derivatives (sugars); and the like. Further, see the materials disclosed and described in U.S. Pat. No. 5,056,211 as well as patents and publications cited therein. Advantages of employing resorbable devices include the fact that, when resorbed, the devices leave behind a healed 'stoma' such that the anastomosis or conduit is completely physiologic, with no foreign body present. It is also possible to produce a device that is comprised of metal or has a metal mesh substructure coated with a polymer or bioabsorbable material, e.g., a blood impermeable membrane as described above. When the device is comprised of metal or includes metal components, the metal must be sufficiently flexible to provide the desired degree of flexibility in the vessels it is used in. The geometric pattern of the metal within the device may be important to obtaining preferred results and may be a woven, sinusoidal or circular metal substructure. The device may be comprised of surgical grade stainless steel or nitinol which has useful superelastic properties. Polymers may be used not only to coat metals but to produce the entire device. Non-resorbable polymers and elastomeric materials such as silicone or fluoropolymers can be produced in the desired size, shape and flexibility.

With respect to the segments or flange portion in particular, materials such as polymers may be used to fabricate the segment or flange in either solid form as a thin section or membrane, or used in a woven or expanded foam state. Suitable polymers include elastomers, such as polyurethane and polysiloxane, or PTFE used in vascular grafts. Elastomers such as polyurethane allow a small amount of local deformation to aid in sealing. Due to the special deformation properties of elastomers, commercial elastomers are typically specified by hardness, with flexural and tensile modulus usually scaling in rough proportion to hardness. Experiments have shown elastomers with a durometer ranging from 80 Shore A (soft) to 55 Shore D (hard) have been suitable for use, with corresponding changes in flange thickness to achieve appropriate mechanical properties for deployment.

Other suitable flange materials include fabrics used for vascular grafts such as Dacron and carbonaceous materials such as carbon fibers. Composite structures for the flange may also be utilized, in the form of reinforcing struts or components to aid mechanical deployment and implant stability. Suitable reinforcing materials for the segment include metals such as stainless steel, titanium, nitinol, structural polymers such as polycarbonate, polythethylene, and polypropylene. For further stability, the tubular member may be reinforced with a wound wire or other anti-kinking means.

Any or all of the different materials can be coated with a desired compound or drug. The device blood-contacting surface may be lined with endothelial cells. These cells may be cells extracted from the patient the device is being placed in or from a tissue culture of such cells from another patient. Further, the materials may be embedded with any desired compound or drug which provides desired properties to the device. Useful coatings include drugs such as heparin which may be used alone or in combination with hydrogels or hydrophilic compounds. Any anticoagulant compound may be extremely useful as a coating on devices inserted into the vessels of the cardiovascular system.

A device of the invention may be comprised of any material that is appropriate for localized delivery of various compounds including compounds such as antiplatelet agents, calcium agonists, antiinflammatory compounds, antiproleferative drugs, hypolipidemic agents, and angiogenic factors. The device may be comprised such that all or any of these compounds are coated on the surface of the material, embedded within it or incorporated within a chamber (not shown) of the device so that the compound is released in a metered fashion from the device to the area surrounding the anastomosis.

In certain preferred embodiments, the devices are bioprosthetic devices fabricated from tissue, e.g., autologous, allogenic or xenogenic tissue. The tissue may be any convenient tissue that is capable of providing the appropriate flexibility and rigidity to the final bioprosthetic device, e.g., after one or more processing or "fixing" steps, such that the device is capable of serving its intended purpose. In manyembodiments, the tissue is collagenous in nature, by which is meant that a substantial component of the tissue is collagen. Tissues of interest include, but are not limited to: pericardium, connective tissues, e.g., dura matter, tendons, ligaments, skin patches, mucosal patches, omentum, arteries, veins and the like, where the tissue is generally mammalian in nature, where specific species of interest include cow, horse, pig, sheep, primates, e.g., monkeys, baboons, and humans, where in many embodiments, the tissue will be of human origin, e.g., where the tissue may be an auto- or allograft, e.g., from a live person or a cadaver. Following harvest of the suitable tissue, the tissue is cut or shaped to the desired configuration, where the tissue may be manually shaped or shaped at least partially with the help of specialized tools/machines, e.g., die cutting devices, etc. At some point during preparation, the tissue may be processed to provide for one or more desirable attributes, where processes of interest include cross-linking, immunogenicity minimization modification, e.g., by fixation, modification to reduce enzymatic attack, and the like. Representative bioprosthetic materials and methods for their manufacture which may be readily adapted by those of skill in the art to fabricate anastomotic devices according to the present invention are described in U.S. Pat. Nos. 6,106,555; 6,093,530; 6,008,292; 5,984,973; 5,855,617; 5,609,600; 5,595,571; and the like, the disclosures of which are herein incorporated by reference.

Anastomotic Methods

As indicated above, the devices and methods of the subject invention may beemployed to join any two or more vessels together, where the subject methods are particularly suited for joining vessels together that are located, or are to be located, in a living animal, e.g., the human body. The subject devices and methods are particularly suited for use in joining vascular vessels, where any type of vascular vessel may be joined to another vessel, where representative types of vascular vessels include, but are not limited to: coronary vessels, peripheral vessels, neurovascular vessels, etc. As such, the subject devices and methods can be used in a variety of applications, including coronary bypass applications, including both proximal and distal anastomoses, peripheral vascular bypass applications, neurovascular bypass applications, and the like. The vessels that are joined may be naturally occurring vessels, e.g. autologous donor to a graft, etc., or synthetic/fabricated vessels, e.g., synthetic vein, artery grafts, prosthetic tubes, etc. In those embodiments where the subject devices are intended to join vascular vessels together, e.g., human vascular vessels, they are dimensioned or shaped so as to work with the target vessels to be joined, e.g., they are shaped or dimensioned such that they fit within the human vessels, e.g. arteries, veins, to be joined.

The device of the invention in any of its embodiments may be inserted without the use of special surgical tools. Specifically, the device may be inserted manually (i.e., using the surgeon's fingers alone) or in combination with other surgical equipment normally used when operating on a patient. The subject methods may be performed intravascularly or extravascularly, i.e., an intravascular or extravascular approach may be employed with the subject devices. In intravascular methods, the device is delivered to the anastomotic site through a vessel, e.g., the donor or host vessel, where any convenient delivery means may be employed, including the delivery sheaths and devices described infra. For extravascular protocols, the device is introduced to the anastomotic site from outside of the vessel.

The present invention provides for the following general steps for interconnecting vessels using a flexible device of the present invention in which a first member is connected to a second member along a periphery of an opening in the first member and in the second member. First, the first member is bent to a reduced size, and then inserted into an opening of a vessel. When released, the first member expands to its original configuration and conforms to an inner surface or circumference of the vessel. The second member is inserted into the opening made in a second vessel. The surgeon then has the option to further secure the vessels to the device and to each other, or in other protocols, to secure the second vessel to the second member. This can be done by applying an adhesive between a surface of the member and a surface of the vessel, or by using a securement member (such as a cuff, collar or ring) positioned about the two.

More particularly, for side-to-side anastomoses, the side-to-side devices described above are employed to join two vessels in a side-by-side relationship, e.g., as shown in FIG. 2. In these methods, openings or slits are first prepared in the sides of the graft and host vessels. The openings or slits are sufficiently large to allow insertion of the first or second segments in a constricted or bent configuration, but are small enough such that the first or second segment cannot readily be pulled out of the vessel through the opening upon deployment of the segment and the first and second segments provide a leak free seal around the openings or slits. In many embodiments, the openings will be slits ranging in length from about 2 to 8 mm, usually from about 4 to 6 mm. Next, the first and second segments are inserted through the openings and allowed to deploy in a manner that produces a sealing relationship between the upper surface of the segment and the inner wall of the vessel. The above steps result in the establishment of fluid communication between the lumens of the host and graft vessels such that the two vessels are anastomosed to each other in a side-to-side configuration.

The end-to-side anastomosis protocols of the present invention are somewhat analogous to the side-to-side protocols and summarized above. In the end-to-side protocols, an opening or slit is prepared in the side of the host vessel, as described above. Next, the first segment of the end-to-side device is inserted through the opening and allowed to deploy. Depending on the particular protocol employed, the tubular member of the device may or may not have been pre-secured to the open end of the graft vessel. To secure the open end of the graft vessel to the tubular member, the open end of the graft vessel is placed over the tubular end of the device in a manner that provides for a secure positioning of the graft vessel over the tubular member. In certain embodiments, the dimensions of the tubular member are slightly larger than the inner diameter of the graft vessel such that the open end of the graft vessel must be stretched to slide it over the tubular member and, upon release of the stretching force, constricts with sufficient force to secure it to the tubular member. In other embodiments, a securing means may be employed to secure the end of the graft vessel to the tubular member. Securing means of interest include bioglues, sealing rings that can be slid the graft vessel/tubular member structure followed by constriction to secure the vessel to the tubular member, i.e., annular or ring securing means that move from a first expanded to a second constricted position, such as those described in U.S. Pat. No. 6,056,762, the disclosure of which is herein incorporated by references, ties, loops or lashes to secure the vessel to the tubular member, and the like.

Figure 6A:
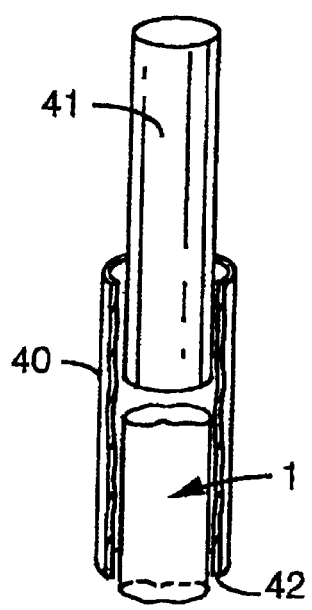
FIG. 6 includes FIGS. 6A, 6B and 6C each of which show an alternative side-to-side embodiment of the invention being delivered by a surgical dispenser and inserted into a vessel with FIG. 6A showing the device almost completely inserted within the surgical dispenser lumen, FIG. 6B showing the device partially extruded from the surgical dispenser lumen and FIG. 6C showing the device completely extruded.
Figure 6B:
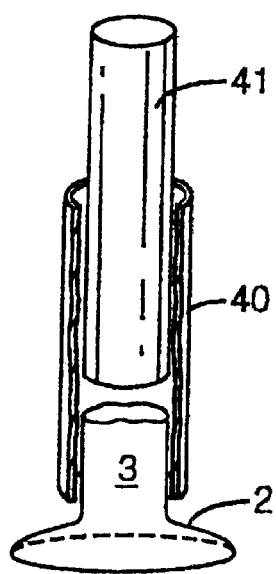
Figure 6C:
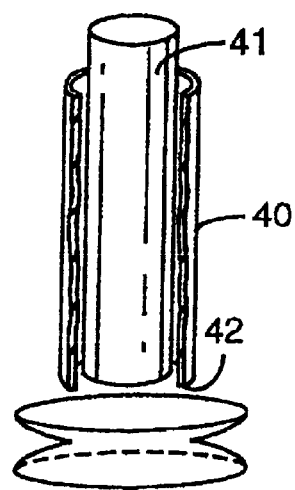

As indicated above, any suitable delivery protocol may be employed. In connection with intravascular delivery of the device, it may be desirable to provide the device of the invention using a catheter or surgical dispenser through which the device is moved and inserted. FIGS. 6A, 6B and 6C illustrate a simple representation of how the device can be inserted using a surgical dispenser for bypass surgery with direct access to the heart.

The device such as the devices shown in FIGS. 1, 3, 5, 9, 10 and 11 as well as any alternative embodiment of these will be referred to as device 1 as shown in FIG. 6A. The device 1 is placed within the delivery sheath 40. Because the device is flexible, it can be compacted to a relatively small shape. After being placed in the delivery sheath 40, the push plunger 41 is used to force the device 1 through the delivery sheath 40. The end 42 of the delivery sheath 40 is preferably first placed within an opening of a vessel. After being placed in that opening the push plunger 41 is used to force the first segment 2 of the device 1 out of the delivery sheath 40 as shown in FIG. 6B. Thereafter, the end 42 of the device is withdrawn from the opening, of the first vessel and placed in the vicinity of an opening of a second vessel. At this point, the plunger 41 is forced forward until the second segment 3 of the device 1 is extruded from the delivery sheath 40. The surgeon may ease the insertion by manipulating the vessels and the device 1 for optimum placement. At this point, the device 1 is in place interconnecting two vessels (See FIG. 2).

Figure 7C:
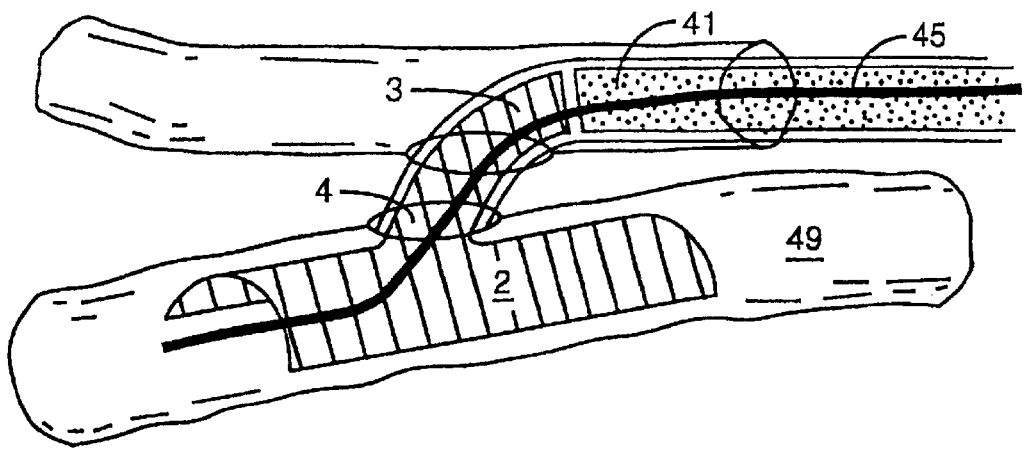
FIG. 7 includes FIGS. 7A, 7B, 7C, 7D and 7E each of which show a step of putting of an alternative side-to-side embodiment of the invention in place using a catheter and guidewire with FIG. 7A showing the device within the catheter and a guidewire in place, FIG. 7B showing the device moved toward the opening in the vessel guided by the guidewire, FIG. 7C showing the device partially inserted, FIG. 7D showing the device completely inserted into two vessels thereby interconnecting those vessels and FIG. 7E showing the catheter withdrawn.
Figure 7D:
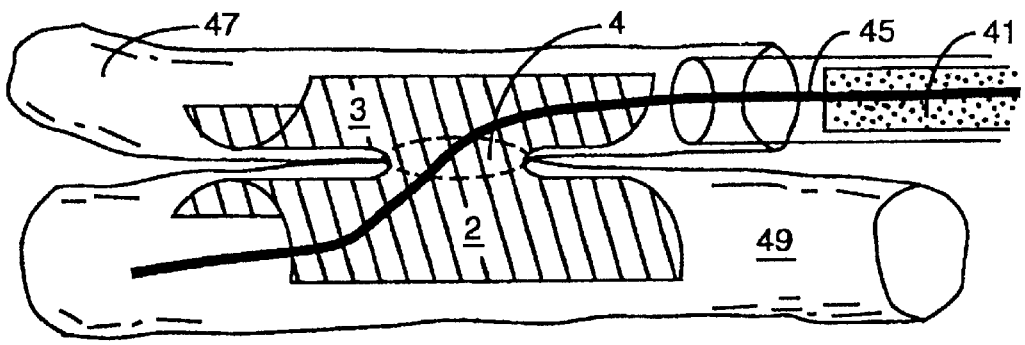
Figure 7E:
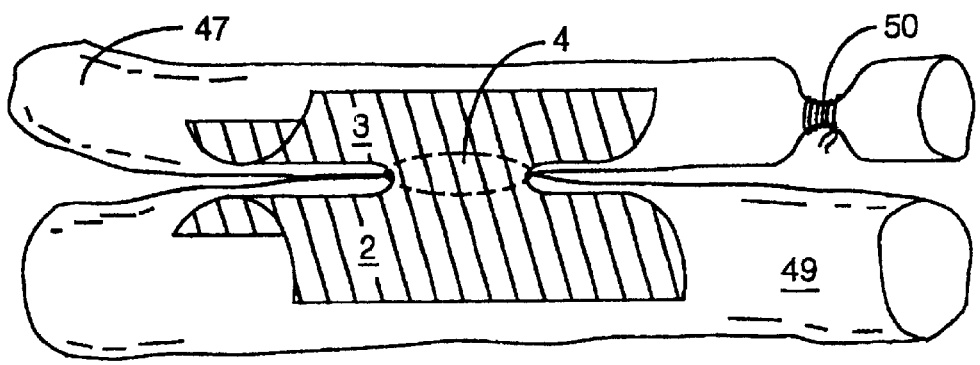

For a less invasive approach, a catheter and a guidewire delivery system can be used as is shown in FIGS. 7A–E. Device 1 is delivered by the catheter through the graft vessel 47. In this embodiment the device 1 is placed within the delivery sheath 40 in a manner such that guidewire 45 is led through the opening 4 (see FIG. 1) of the device. The guidewire 45 is then inserted within an opening 46 of a graft vessel 47. At this point, the push plunger 41 is used to force the device 1 forward toward the opening 46 as is shown in FIG. 7B. The guidewire then leads the catheter into an opening 48 of a native vessel 49 as shown in FIG. 7B. The device 1 as shown in FIG. 7B is now in position for insertion into the opening 48 of the native vessel 49. The push plunger 41 is then moved forward as shown in FIG. 7C. This causes the first segment 2 of the device 1 to be inserted into the opening 48 of the native vessel 49. Upon being inserted into opening 48, the first segment 2 expands into its original shape. When this is completed, the delivery sheath 40 is positioned relative to the opening 46 of the graft vessel 47 and the push plunger 41 is moved forward to force the second segment 3 of the device 1 out of the delivery sheath 40. The second segment 3 also expands into its original shape upon being forced out of the delivery sheath 40. When this is accomplished the result is shown in FIG. 7D. At this point the device 1 is completely inserted and the vessels 47 and 49 are interconnected by the opening 4 of the device 1. Thereafter the delivery sheath 40, push plunger 41 and guidewire 45 may be withdrawn completely from the patient.

One aspect of the invention is a device such as the device 1 of FIG. 1 or device 33 of FIG. 5 loaded into a catheter delivery system of the type shown in FIGS. 7A–7E. The device 1 is loaded into the delivery sheath 40 so that the guidewire 45 goes through the opening 4. The combination of the device 1 and delivery sheath 40 can be conveniently sold as a unit for performing an anastomosis. Such a combination product provides the surgeon with a device properly matched in size with an insertion catheter.

Figure 8A:
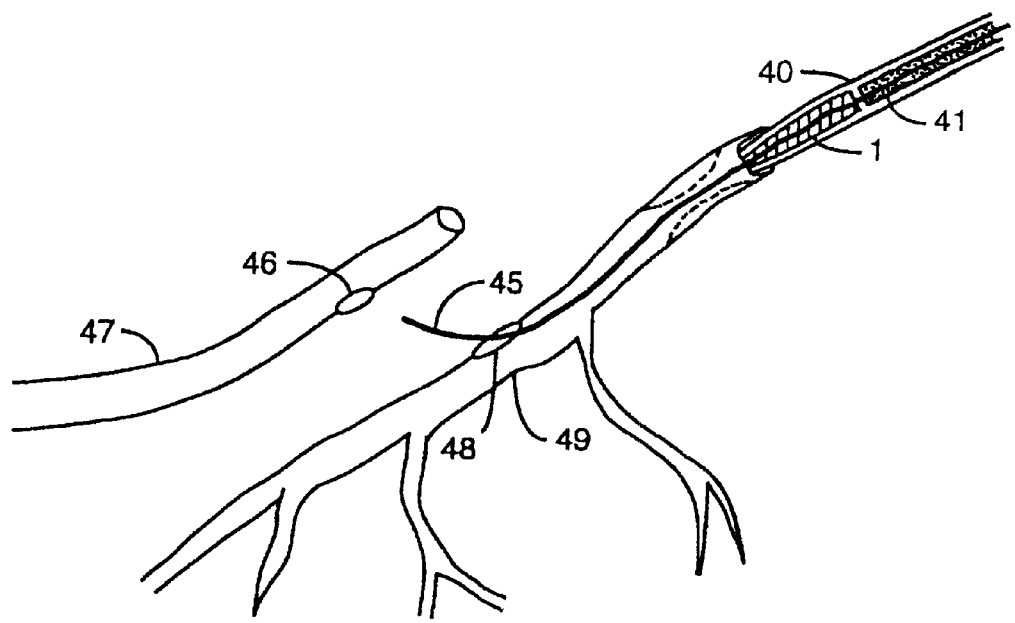
FIG. 8 includes FIGS. 8A, 8B and 8C which show three steps of a device of the type shown in FIG. 1 being inserted into and interconnecting two vessels with FIG. 8A showing the device in the catheter, FIG. 8B showing a guidewire inserted in the vessel opening and FIG. 8C showing the device in place.
Figure 8B:
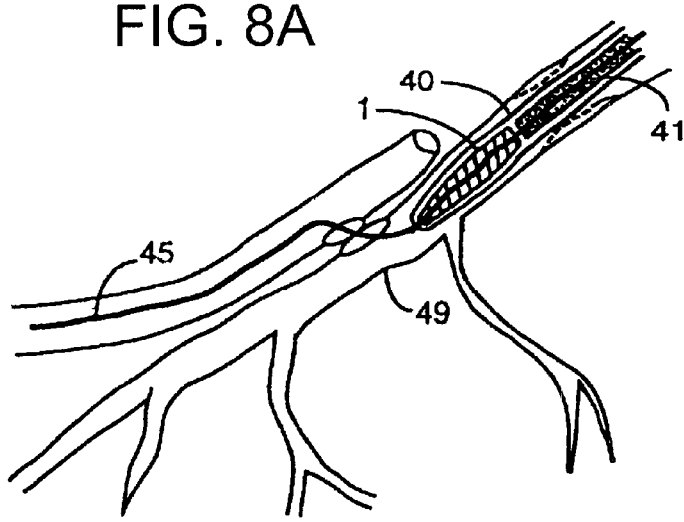
Figure 8C:
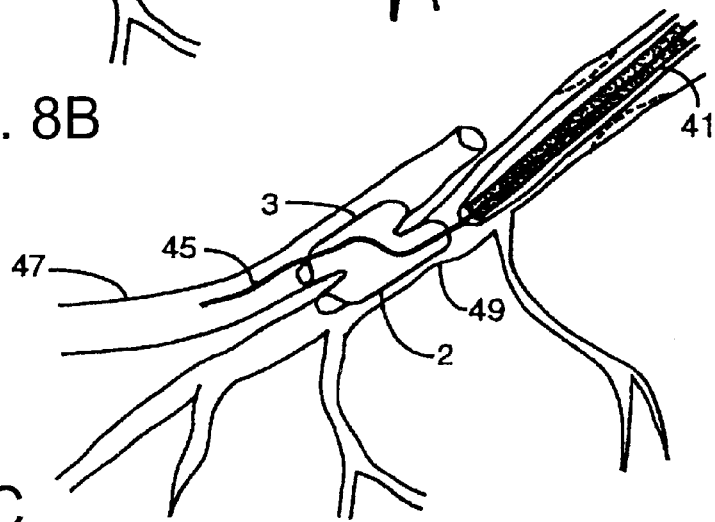

Another embodiment of the catheter insertion procedure is shown in FIGS. 8A, 8B and 8C. In this embodiment the device 1 is delivered using a catheter through the native vessel 49. Specifically, the delivery sheath 40 has the device 1 loaded within it. The device 1 is loaded into the delivery sheath 40 in a manner such that the guidewire 45 goes through the opening 4 of the device 1. Further, the push plunger 41 is positioned within the delivery sheath 40. The end of the delivery sheath 40 is placed within the native vessel 49 and the guidewire 45 is moved through the native vessel 49 and out of the opening 48 of the native vessel 49 as shown within FIG. 8A. Thereafter, the catheter is moved forward and the guidewire 45 is moved into the opening 46 of the graft vessel 47 (see FIG. 8B). Thereafter, the push plunger 41 is moved forward so that the device 1 forced out of the catheter 40. The first segment 3 of the device 1 enters the opening 46 of the graft vessel 47 and the second segment 2 of the device 1 remains within the native vessel 49 (see FIG. 8C).

After insertion and completion of the anastomosis the free end of the vessel 47 is tied off in a manner as shown within FIG. 2. It may be necessary to further expand the device by the use of a balloon catheter not very differently than a post dilatation of an angioplasty stent. This may help fully expand the device and enhance the sealing and connecting properties of the device. It may also be necessary to utilize stay sutures to stabilize the graft near the heart. These sutures are placed through fat or tissue surrounding the vessel in order to provide additional stability to the anastomosis. This is normally done when grafting the internal mammary artery to the coronaries but may be necessary in some cases using this device in order to prevent the vessels 49 and 47 from being inadvertently separated from each other.

In certain embodiments, it may be desirable to employ a means for holding together the two vessels to be anastomosed during practice of the subject methods. A suitable holding means, i.e., proximator, appositioner, vessel stabilizer, etc., will comprise a means for holding the donor and graft vessels, e.g., the coronary artery and the IMA, together in a sufficiently close relationship, e.g., in adjacent relationship, so that the device can join the vessels as described above.

Stopped Heart/Beating Heart

The device of the present invention can be used to interconnect vessels or more specifically complete an anastomosis while the patient's heart is beating or after the patient's heart has been stopped. Beating heart procedures can be carried out by making a variety of different types of initial incisions which could include a sternotomy where the patient's sternum is bisected or by making smaller incisions and utilizing minimally invasive surgical devices and methods (see Benetti, F. in U.S. Pat. No. 5,888,247). After the necessary incisions are made the heart is stabilized using a stabilizer device. Thereafter the device of the invention is inserted by one or more different means described herein. Specifically, the first segment of a flexible device is inserted by bending the device and moving it into an opening in a first vessel. After bending the device and inserting it within the vessel it is released and the first segment of the device resumes its original configuration where the device conforms to an inner intravascular surface of the first vessel. The first segment of the device includes an opening and is connected to a second segment of the device along the periphery of that opening. The second segment of the device is then bent and moved into an opening of a second vessel. Thereafter the device is released and it resumes its original configuration and conforms to the interior wall of the second vessel.

The device can also be used in a stopped heart situation. Many of the different types of initial incisions mentioned above or others can be used to access the patient's chest cavity. A suitable graft vessel is harvested from the patient. Thereafter the patient's heart is stopped using a suitable cardioplegia. Thereafter, the steps referred to above with respect to insertion of the device are carried out. Although the present invention can be used in connection with a stopped heart procedure one of the advantages of the present invention is the ease of manipulation of the device in order to carry out an anastomosis. Because of the simple efficient manner in which the device of the invention can be manipulated and inserted it can generally be carried out while the patient's heart is beating.

Robotic Assist Intervention

The device can be used when robotic assist devices are utilized by the surgical staff. Robotic assist device surgery is typically performed by the surgeon through the use of robotic arms. The use of the robotic arms scales the motion of the surgeon and filters out unwanted tremors. This allows the surgeons to perform the surgery through smaller incisions and in more constricted spaces. Examples of such systems are the ones marketed by Intuitive Surgical Systems as described in U.S. Pat. No. 5,855,583.

Surgical Access and Visualization

The device and the catheter delivery systems can be used during hybridprocedures where surgical procedures are combined with interventional cardiology techniques. Such procedures use fluoroscopy to visualize and position the catheter delivery systems. The catheter is normally placed through femoral or radial access. Direct surgical access to the heart is typically achieved via small incisions in the chest or abdomen. A single or multiple trocar ports or a minimally invasive small retractor is placed in these incisions. An endoscope may be used to aid in visualization and/or deliver the catheter when employed to deliver the device.

The device can also be used in complete percutaneous procedures where no direct access to the heart is available to the physicians.

Stabilizing Device Implantation

Each embodiment of the invention is designed in a manner such that it does not require additional devices, sutures, staples or other materials to hold the device in place. Preferably, the first (and second) segment(s) of the device are joined and configured in a manner such that once the device is in place the segments will apply sufficient force against the interior walls of the vessel to securely hold the device in place aided by the action of intraluminal pressure. After the device has been held in place for significant periods of time, the vessels will naturally develop a new intimal layer and fuse through normal wound healing. At this point the device may no longer be needed and could, if so designed, begin dissolving.

In certain embodiments and certain situations it may be desirable to add additional means of holding the device in place. One addition holding means of interest includes biocompatible glues and adhesives. The glue could be applied after the device is implanted or placed on the device prior to implantation. Any biocompatible glue could also include other drugs such as growth factors that would aid in causing the vessels to grow together in the desired manner. Another means of interest is an annular or ring connector that can move from a first expanded to a second constricted position, such as those described in U.S. Pat. No. 6,056,762; the disclosure of which is herein incorporated by reference.

Kits

Also provided are kits that at least include one device according to the subject invention, where in many embodiments the kits may include two or more devices having varying sizes so as to provide the surgeon or other health care practitioner the convenience and security of having a device with the correct size for a particular patient. The kits may further include other tools such as delivery devices, (e.g., a delivery catheter, loaded delivery device, etc.), proximator or sizing devices for determining the appropriate size of the device to be used, and the like, as described above, which devices find use in performing an anastomosis with the device present in the kit. The kit may comprise only one anastomotic device of the invention having a single-size segment(s) which may be readily usable for larger vessels but not for smaller ones. This kit may further include a stamping or cutting fixture and mechanism for trimming the segment to achieve an appropriate size so as to fit into a smaller vessel. Each of the tools of the present invention may also have more than one function. For example, both cutting and delivery functions may be included in a single tool increasing the ease of the procedure, eliminating the cost of another tool and reducing the procedure time. The subject kit may contain a device comprising a single size intravascular segment of sufficient size to be applicable to the largest vessels. The kit may comprise a stamping or cutting fixture and mechanism used to trim the size of the intravascular segment in an appropriate manner so as to be able to fit into smaller vessels.

The subject kits may also include securing or reinforcement means, e.g., biocompatible glues/adhesives, hemostatic rings, etc. In addition, the subject kits typically include instructions for using the devices in methods according to the subject invention. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way if illustration and not by way of limitation.

EXPERIMENTAL

Experimental Examples

An experiment was conducted to test the ease of insertion, sealing properties and retention ability of the segments/flanges of the anastomotic devices of the present invention. Various embodiments of the segments/flanges were implanted into a vessel of a swine weighing 39.2 kg. Vessel having diameters of 2, 3 and 4 mm were used as implant vessels due to their similiarity in size to average human coronary arteries. Seven segments were used, all made of a silicone-urethane copolymer (Polymer Technology Group, Pursil 80A) and having a semi-ellipsoidal shape with short and long axis dimensions of 9 by 15 mm. The segments had varying thicknesses ranging from 100 to 380 microns ($100 \times 10^{-3}$ to $380 \times 10^{-3}$ mm). Prior to implant, a suture was secured to the center of each segment to aid in testing the stability and the ability of the segments to keep from dislodging from the arteriotomy. The swine was placed under general anesthesia and, once adequately sedated, a pressure line was placed in its left femoral artery in order to continuously monitor the swine's blood pressure. For each implant vessel, approximately 5 cm of the vessel's length was exposed and isolated. Conventional bulldog clamps were then placed on the exposed vessel, one on each side of the arteriotomy site, to occlude the vessel during implantation of the various devices. An arteriotomy was then cut in the exposed section of vessel between the bulldog clamps. Each of the seven segments was individually inserted into the artery between 10 and 20 minutes during which time observations were made and tests were conducted. No sutures or glues were used to augment the sealing or physical stability of the implanted segments. Blood pressure was manipulated pharmacologically (with Levophed) to create low and high-pressure environments as desired. Ease of insertion and observations for leakage from the arteriotomy site were recorded. A pull test was conducted on each segment by tugging on the centrally placed suture to determine the segments propensity for dislodgment from the vessel. The table below summarizes the results obtained from the experiment:

| Segment Thickness | Vessel size | Min–Max BP | Ease of Insertion | Sealing & Leakage | Pull Test (tug strength & dislodgment) |
|---|---|---|---|---|---|
| 1. 380 microns (380 × $10^{-3}$ mm) | 3 mm | 70/12 to 250/110 | High | Good | Strong; no dislodgment |
| 2. 100 microns (100 × $10^{-3}$ mm) | 3 mm | 64/12 to 230/109 | Moderate | Good | Easy; dislodged |
| 3. 150 microns (150 × $10^{-3}$ mm) | 3 mm | 58/17 to 210/109 | High | Good | Fair; dislodged |
| 4. 200 microns (250 × $10^{-3}$ mm) | 3 mm | 68/21 to 210/109 | High | Good | Very strong; minor leakage but no dislodgment |
| 5. 250 microns (250 × $10^{-3}$ mm) | 3 mm | 58/18 to 220/110 | High | Excellent | Very strong; some leakage and slipping but no dislodgment |
| 6. 300 microns (250 × $10^{-3}$ mm) | 4 mm | 59/20 to 198/110 | High | Excellent | Very strong; some leakage and slipping but no dislodgment |
| 7. 250 microns (250 × $10^{-3}$ mm) | 2 mm | 66/19 to 198/112 | High | Excellent | Very strong; no leaks or dislodgment |

Overall, the experiment showed that segments/flanges made of polyurethane polymer and having a thickness in the range from 100 to 380 microns ($100 \times 10^{-3}$ to $380 \times 10^{-3}$ mm) produced a good arteriotomy seal under normal physiological conditions. The thinner segments provided good sealing function but were less physically stable once in-situ. A range of thicknesses for optimally handling and implanting the segments appeared to be in the range of 250 to 300 ($250 \times 10^{-3}$ to $300 \times 10^{-3}$ mm) microns with a material having the physical properties utilized in this experiment.

It is evident from the above description and results that the subject invention provides important new anastomotic devices and procedures which overcome a number of disadvantages currently encountered in the field of anastomosis. The subject devices are easy to use and can provide for vessel joinder with out the use of sutures, staples, glues or other holding means. In addition, the subject devices are substantially atraumatic and provide for rapid healing. As such, the subject invention represents a significant contribution to the field.

The instant invention is shown and described herein in what is considered to be the most practical, and preferred embodiments. It is recognized, however, that departures may be made there from, which are within the scope of the invention, and that obvious modifications will occur to one skilled in the art upon reading this disclosure.

What is claimed is:

1. A device for performing an anastomosis wherein the device is implantable to a site within a vessel of a subject through an artificially-made opening in the vessel, comprising:

a first segment comprised of a compliant material and having a configuration whereby the first segment is constrictable to a size sufficient to fit through the artificial opening and is expandable to be securely and permanently self-retained within the vessel upon implantation, the first segment comprising:

a vessel-contacting surface and a lumen-facing surface, wherein, upon implantation of the first segment, the vessel-contacting surface is adapted to readily conform to and seal with the inner surface of the conduit and wherein the lumen-facing surface is adapted to utilize the internal conduit pressure exerted thereon to form a substantially fluid-tight seal between the vessel-contacting surface and an inner surface of the conduit; and a second segment for implantation into a second vessel.

2. The device of claim 1 wherein the second segment comprises the same configuration and material as the first segment.

3. The device of claim 1 wherein the second segment comprises a different configuration and/or a different material as the first segment.

4. The device of claim 1 wherein the first and the second segments are in fluid communication with each other.

5. The device of claim 4 further comprising a flow opening between the first and second segments.

6. The device of claim 5 wherein the flow opening comprises a flow channel extending between the first and second segments.

7. The device of claim 1 wherein the first and second segments are in a unitary configuration.

8. The device of claim 1 comprised of two pieces, a first piece comprising the first segment and a second piece comprising the second segment.

9. The device of claim 8 further comprising a securement member for securing the two pieces in a sealed engagement thereby forming a fluid-tight channel between first and second segments.

10. A device for performing an anastomosis wherein the device is implantable to a site within a vessel of a subject through an artificially-made opening in the vessel, comprising:

a first segment having a configuration and comprised of a compliant material whereby the first segment is constrictable to a size sufficient to fit through the artificial opening and is expandable to be securely and permanently self-retained within the vessel implantation, and wherein the first segment comprises a vessel-contacting surface and a lumen-facing surface, wherein, upon implantation of the first segment, the vessel-contacting surface is adapted to readily conform to and seal with the inner surface of the conduit and wherein the lumen-facing surface is adapted to utilize the internal conduit pressure exerted thereon to form a substantially fluid-tight seal between the vessel-contacting surface and an inner surface of the conduit; and a tubular member extending radially from the first segment for implantation into a graft vessel.

11. The device of claim 10 wherein the tubular member is comprised of the same material as the first segment.

12. The device of claim 10 wherein the tubular member is comprised of a material different from the first segment.

13. The device of claim 10 wherein the first segment and the tubular member are in fluid communication with each other.

14. The device of claim 13 further comprising a flow opening between the first and second segments.

15. The device of claim 10 wherein the first and second segments are in a unitary configuration.

16. The device of claim 10 comprised of two pieces, a first piece comprising the first segment and a second piece comprising the tubular member.

17. The device of claim 16 further comprising a securement member for securing the two pieces in a sealed engagement thereby forming a fluid-tight channel between the first segment and the tubular member.

18. The device of claim 10 wherein the tubular member has an outer diameter that approximates the inner diameter of the graft vessel.

19. The device of claim 18 wherein the tubular member has a length in the range from about 10 to 20 mm.

20. The device of claim 10 wherein the tubular member extends substantially perpendicular to the first segment.

21. The device of claim 10 wherein the tubular member extends at an angle from the first segment.

22. The device of claim 21 wherein the angle is in the range from about 1° to 90°.

23. The device of claim 22 wherein the angle is in the range from about 5° to 90°.

24. The device of claim 23 wherein the angle is in the range from about 20° to 90°.

25. The device of claim 10 wherein the tubular member is straight along its entire length.

26. The device of claim 10 wherein the tubular member comprises a bend along its length wherein the bend defines an angle in the range from about 90° to 179°.

27. A method of interconnecting conduits in a patient using a flexible anastomosis device having a first member connecting to a second member along a periphery of an opening in the first member and the second member, comprising the steps of:

bending a flexible first member of the flexible anastomosis device to a reduced size, the first member having a flexible surface which conforms to an inner surface of a first conduit of a patient;

inserting the bent first member into an opening of the first vessel, wherein upon being inserted into the first conduit, the bent first member expands conforming to the inner surface of the first conduit; and inserting the second member into an opening of the second conduit.

28. The method of claim 27, further comprising securing the second conduit to the second member.

29. The method of claim 28, wherein the step of securing comprises applying an adhesive between a surface of the second member and a surface of the second conduit.

30. The method of claim 28, wherein the step of securing comprises using a securement member to secure the second conduit to the second member.

31. The method of claim 27, wherein the first member and the second member are each inserted manually by a surgeon using only the surgeon's hands.

32. A method of interconnecting vessels in a patient, comprising the steps of:

inserting a first member of a flexible device by bending the first member and moving it into an opening in a first vessel wherein the first member is configured to an inner circumference of the first vessel and narrows to a flow opening leading to a second member of the device; and inserting the second member by moving it into an opening in a second vessel wherein the second member is configured to an inner circumference of the second vessel, thereby connecting the first vessel and the second vessel via the flow opening between the first member and the second member.

* * * * *